United States Patent
Yamagata et al.

(10) Patent No.: US 7,364,804 B2
(45) Date of Patent: Apr. 29, 2008

(54) PYRAN DERIVATIVE, METHOD FOR MANUFACTURING THE SAME, AND LIGHT-EMITTING ELEMENT CONTAINING THE PYRAN DERIVATIVE

(75) Inventors: Sachiko Yamagata, Kanagawa (JP); Ryoji Nomura, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 490 days.

(21) Appl. No.: 10/917,668

(22) Filed: Aug. 13, 2004

(65) Prior Publication Data

US 2005/0048315 A1   Mar. 3, 2005

(30) Foreign Application Priority Data

Aug. 29, 2003   (JP) .............................. 2003-305664

(51) Int. Cl.
*H05B 33/14*   (2006.01)
*C07D 309/34*   (2006.01)

(52) U.S. Cl. ................. 428/690; 428/917; 544/38; 544/101; 546/99; 548/440; 549/426

(58) Field of Classification Search ................ 549/426; 546/99; 548/440; 544/38, 101; 428/690, 428/917
See application file for complete search history.

(56) References Cited

U.S. PATENT DOCUMENTS

| | | | |
|---|---|---|---|
| 4,146,707 | A | 3/1979 | Van Allan et al. |
| 4,769,292 | A | 9/1988 | Tang et al. |
| 6,649,089 | B2 | 11/2003 | Chang et al. |
| 6,680,132 | B2 | 1/2004 | Shi et al. |
| 7,217,465 | B2 | 5/2007 | Yamagata et al. |
| 2003/0165714 | A1* | 9/2003 | Lee et al. .................. 428/690 |

FOREIGN PATENT DOCUMENTS

| | | |
|---|---|---|
| JP | 2814435 | 10/1998 |
| JP | 2001-19946 | 1/2001 |
| KR | 2003-042284 | 5/2003 |

OTHER PUBLICATIONS

Sato, Y. et al, "Task of Practice: In View of Material Development," Molecular Electronics and Bioelectronics, vol. 11, No. 1, 2000, pp. 86-99 (with English abstract).
Jung, B-J et al, "Pure-Red Dye for Organic Electroluminescent Devices: Bis-Condensed DCM Derivatives," Advanced Functional Materials, vol. 11, No. 6, Dec. 2001, pp. 430-434.
Office Action, Chinese Patent Application No. 200410068600, dated Jun. 29, 2007.

* cited by examiner

*Primary Examiner*—Bernard Dentz
(74) *Attorney, Agent, or Firm*—Cook, Alex, McFarron, Manzo, Cummings & Mehler, Ltd.

(57) ABSTRACT

A light-emitting compound that has excellent carrier transportation properties and that can exhibit long wavelength light is disclosed. Further, a method for manufacturing the light-emitting compound in a high yield is disclosed. The disclosed light-emitting compound is a pyran derivative as represented by general formula 1:

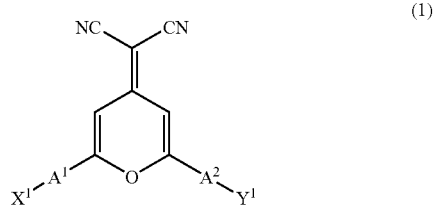

(1)

wherein $A^1$ and $A^2$ are individually a π-conjugated system group having 6 to 16 conjugating carbon atoms; $X^1$ is a dialkylamino group; and $Y^1$ is a diarylamino group or an alkylarylamino group.

20 Claims, 8 Drawing Sheets

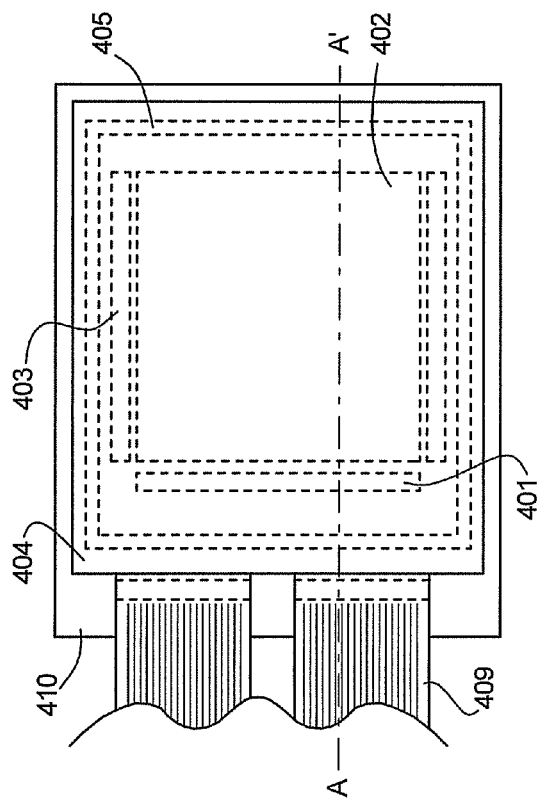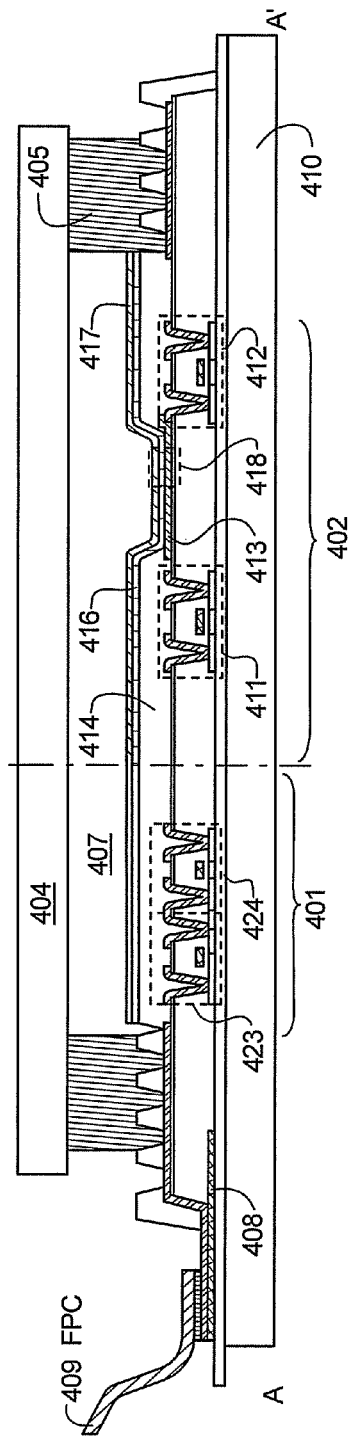

PYRAN DERIVATIVE, METHOD FOR MANUFACTURING THE SAME, AND LIGHT-EMITTING ELEMENT CONTAINING THE PYRAN DERIVATIVE

BACKGROUND OF THE INVENTION

1. Field of the Invention

The present invention relates to a pyran derivative, and more particularly such a pyran derivative that exhibits long wavelength light. Further, the present invention relates to a method for forming the pyran derivative, and a light-emitting element containing the pyran derivative.

2. Related Art

A light-emitting device utilizing light emission from an electroluminescent element (light-emitting element) has been attracted attention as a device for lighting or displaying an image.

In recent years, in the development area for a light-emitting device, the research and development of a light-emitting device capable of displaying a high quality full color image has been accelerated to secure a market of display devices for various information-processing devices such as a TV set or a car navigation system In order to obtain full color image from a light-emitting device, a plurality of regions, each of which exhibits at least three primary colors, is independently provided to let each the region emit light at the right time.

Various methods have been developed to provide the foregoing regions. One method for providing the foregoing regions is that a plurality of layers, each of which is formed by light-emitting compounds producing different colors, is formed at different sites, and a plurality of light-emitting elements including each the layer is independently provided.

In case of using the foregoing method, light-emitting compounds are required to be selected for the respective emission color. Therefore, light-emitting compounds that exhibit light emission at various wavelengths have been developed.

For example, as a material exhibiting reddish emission, a pyran derivative as disclosed in U.S. Pat. No. 2,814,435 (p.7) is developed. Besides, bis-4H-pyran derivatives, or the like are also developed as disclosed in Unexamined Patent Application No. 2001-19946. Generally, it is known that long wavelength light can be obtained by introducing a sterically bulky alkyl group to a molecular structure of light-emitting compounds. The pyran derivatives disclosed in U.S. Pat. No. 2,814,435 and Unexamined Patent Application No. 2001-19946 exhibit long wavelength light by being introduced with a sterically bulky alkyl group to a molecular structure.

However, light-emitting compounds exhibiting long wavelength light (mainly light-emitting compounds exhibiting reddish emission) have low carrier transportation properties, and so driving voltage of a light-emitting element containing the light-emitting compounds tends to be increased. (For example, see Yoshiharu SATO, "The Japan Society of Applied Physics/Organic Molecular Electronics and Bioelectronics", vol. 11, No. 1 (2000), 86-99.) Further, the light-emitting compounds may be difficult to be deposited by vacuum vapor deposition.

SUMMARY OF THE INVENTION

In view of the foregoing, it is an object of the present invention to provide light-emitting compounds that can exhibit long wavelength light. It is another object of the present invention to provide a method for manufacturing the light-emitting compounds in a high yield. It is still another object of the present invention to provide a light-emitting element with low driving voltage for luminescence by using the light-emitting compounds.

One feature of the present invention is a pyran derivative that is represented by any one of the following general formulae 1, 2, 6, 10, structural formulae 18 to 23.

A pyran derivative represented by general formula 1:

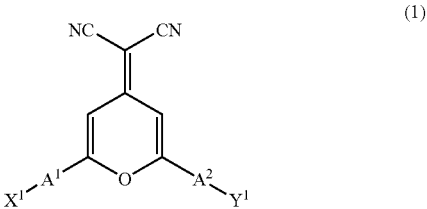

(1)

wherein $A^1$ and $A^2$ are individually a π-conjugated system group having 6 to 16 conjugating carbon atoms; $X^1$ is a dialkylamino group; and $Y^1$ is a diarylamino group or an alkylarylamino group.

A pyran derivative represented by general formula 2:

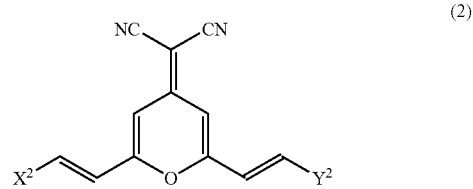

(2)

wherein $X^2$ is represented by general formula 3; and $Y^2$ is represented by general formula 4 or 5.

(3)

wherein $Ar^1$ is an aryl group having 6 to 14 carbon atoms; and $R^1$ and $R^2$, each of which may be the same or different, are individually an alkyl group having 1 to 4 carbon atoms.

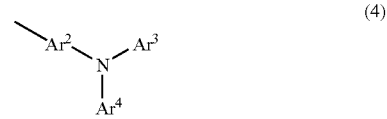

(4)

wherein $Ar^2$ is an aryl group having 6 to 14 carbon atoms; $Ar^3$ and $Ar^4$, each of which may be the same or different, are individually a substituted or unsubstituted aryl group or a heterocyclic group; and a pair of $Ar^2$ and $Ar^3$ and a pair of $Ar^3$ and $Ar^4$ may be bonded directly with each other or bonded with each other via —O— or —S—.

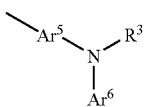
(5)

wherein $Ar^5$ is an aryl group having 6 to 14 carbon atoms; $Ar^6$ is a substituted or unsubstituted aryl group; a pair of $Ar^5$ and $Ar^6$ may be bonded directly with each other or bonded with each other via —O— or —S—; $R^3$ is an alkyl group having 1 to 4 carbon atoms or a hydrogen atom.

A pyran derivative represented by general formula 6:

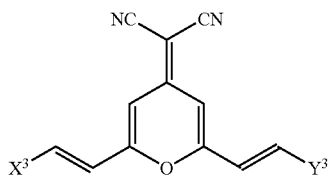
(6)

wherein $X^3$ represented by general formula 7; and $Y^3$ is represented by general formula 8 or 9.

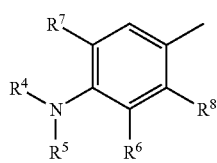
(7)

wherein $R^4$ and $R^5$, each of which may be the same or different, are individually an alkyl group having 1 to 4 carbon atoms; $R^6$ and $R^7$, each of which may be the same or different, are individually an alkly group having 1 to 4 carbon atoms or a hydrogen atom; $R^8$ is an alkoxy group or a hydrogen atom; and a pair of $R^4$ and $R^7$ and a paired of $R^5$ an $R^6$ may be bonded with each other to form a julolidine skeleton.

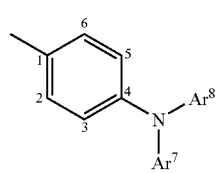
(8)

wherein $Ar^7$ and $Ar^8$, each of which may be the same or different, are individually a substituted or unsubstituted aryl group or a heterocyclic group; 3-position of carbon of a phenyl group may be bonded to the $Ar^7$; a pair of $Ar^7$ and $Ar^8$ may be directly bonded with each other or bonded with each other via —O— or —S—; and Arabic numerals appended to the phenyl group represent position numbers of carbon atoms.

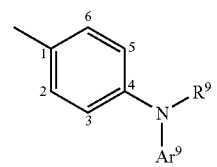
(9)

wherein $Ar^9$ is a substituted or unsubstituted aryl group; 3-position of carbon of a phenyl group may be directly bonded to the $Ar^9$; $R^9$ is an alkyl group having 1 to 4 carbon atoms or a hydrogen atom; and Arabic numerals appended to the phenyl group represent position numbers of carbon atoms.

A pyran derivative represented by general formula 10:

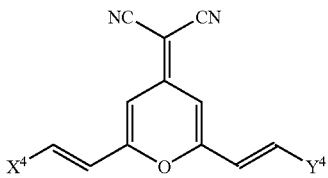
(10)

wherein $X^4$ is represented by general formula 11 or 12; and $Y^4$ is represented by any one of general formulae 13 to 17.

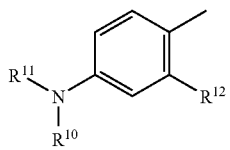
(11)

wherein $R^{10}$ and $R^{11}$, each of which may be the same or different, are individually an alkyl group having 1 to 4 carbon atoms; and R12 is an alkoxy group having 1 to 6 carbon atoms or a hydrogen atom.

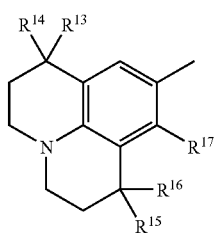
(12)

wherein $R^{13}$ to $R^{16}$ are individually an alkyl group having 1 to 4 carbon atoms or a hydrogen atom; and $R^{17}$ is an alkoxy group having 1 to 6 carbon atoms or a hydrogen atom.

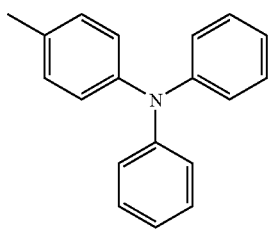
(13)

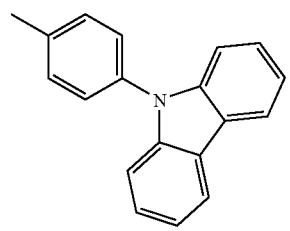
(14)

-continued

(15)
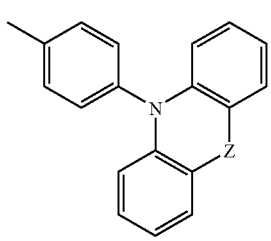

wherein Z is an oxygen atom (O) or sulfer atom (S).

(16)
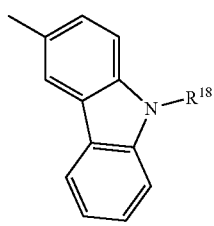

wherein $R^{18}$ is an alkyl group having 1 to 4 carbon atom or a hydrogen atom.

(17)
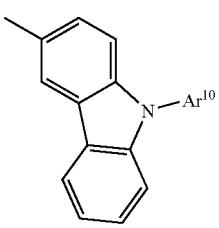

wherein $Ar^{10}$ is an aryl group having 2 to 14 carbon atoms or heterocyclic group.

The foregoing pyran derivative according to the present invention has carrier transportation properties, and exhibits long wavelength light of from 560 to 700 nm. This arises from the fact that the pyran derivative according to the present invention has both hole transportation properties derived from an arylamine skeleton, and a property of exhibiting long wavelength light derived from electron repelling properties of an alkylamine skeleton. Furthermore, the pyran derivative according to the invention can be formed into a film by vapor deposition despite that it is introduced in the alkylamine skeleton with a sterically bulky alkyl group having a julolidine skeleton. This is due to the fact that heat resistance properties are improved by introducing to a substituent bonded to 2-position (or 6-position) of 4H-pyran. By introducing a sterically bulky alkyl group, further long wavelength light can be achieved. Further, long wavelength light is resulted to reddish emission with good color purity.

The followings are specific structural formulae 18 to 58 for a pyran derivative according to the invention. However, the present invention is not limited to the following formulae.

(18)
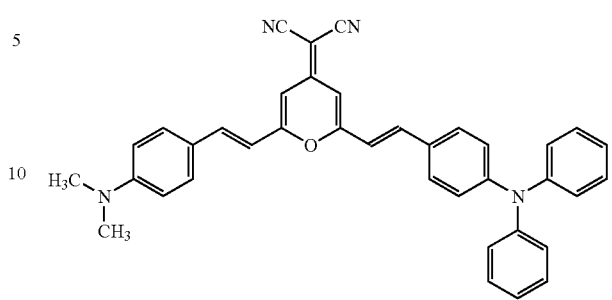

(19)
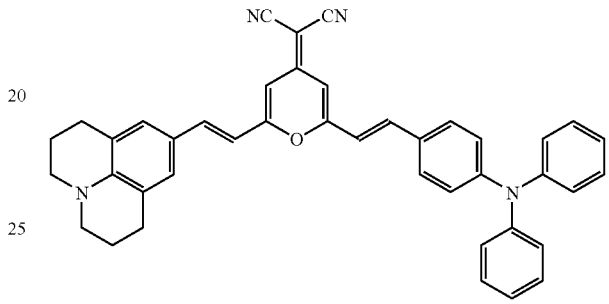

(20)
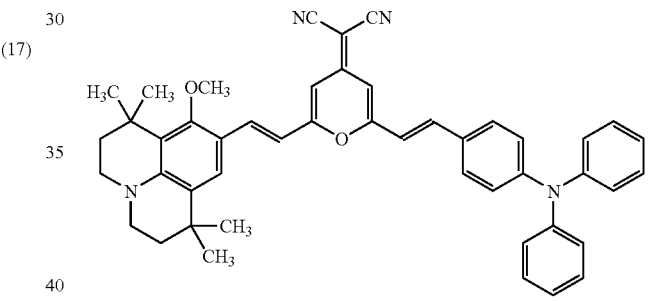

(21)
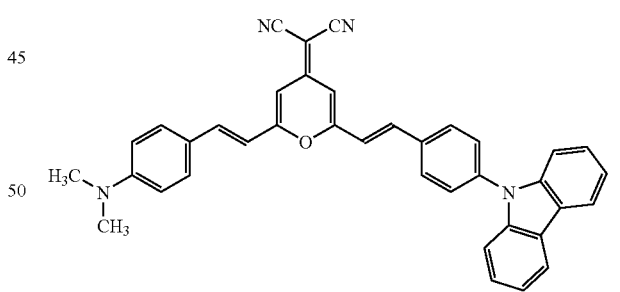

(22)
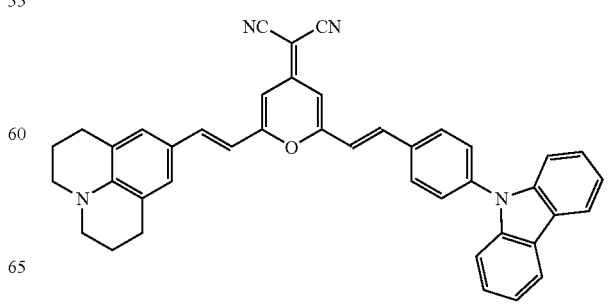

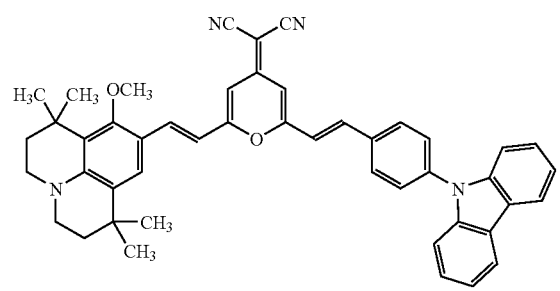
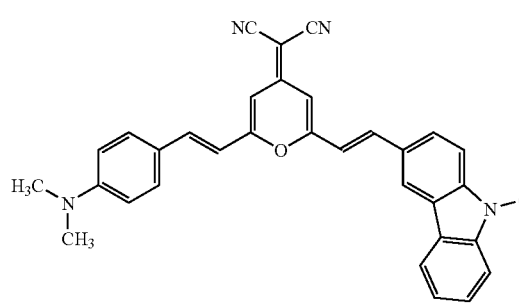
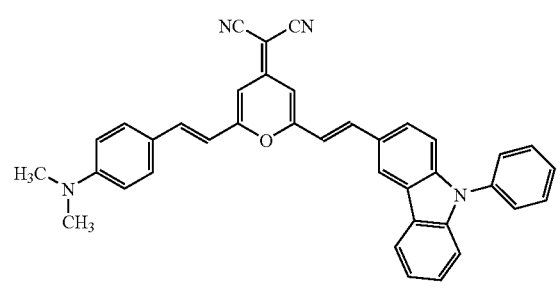
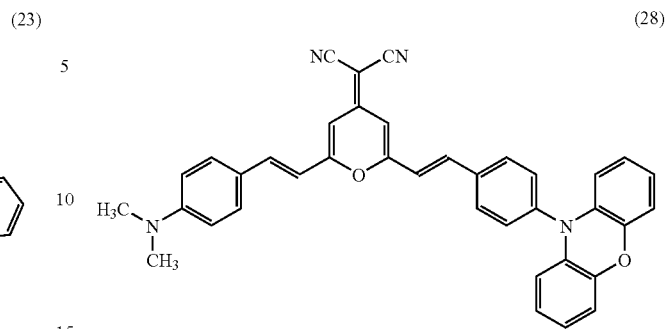

-continued
(33)
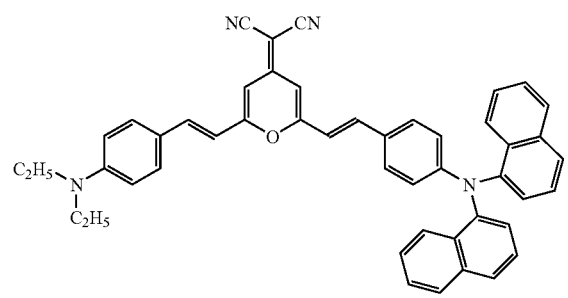
(34)
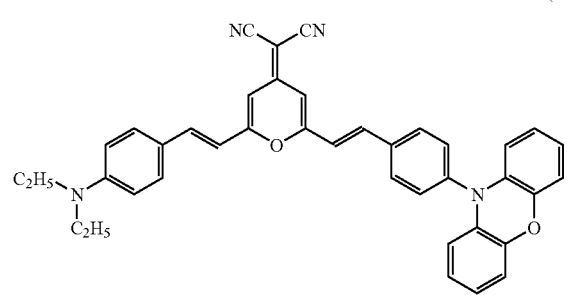
(35)
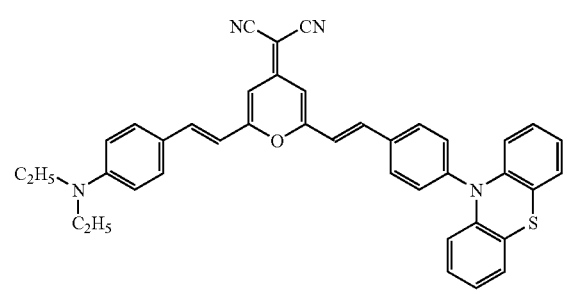
(36)
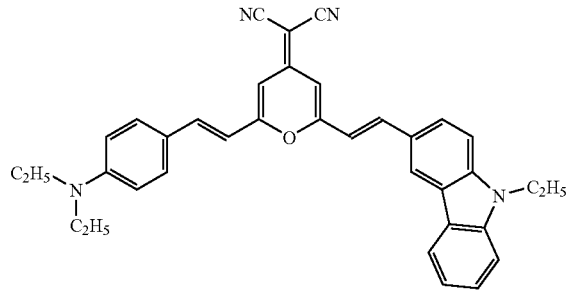
(37)
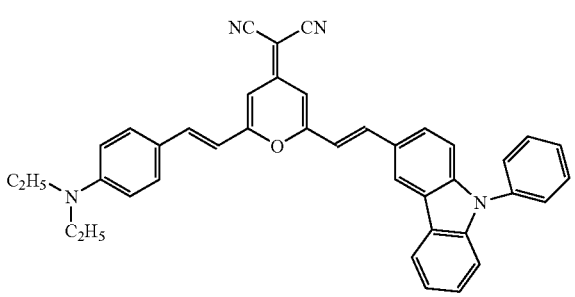
-continued
(38)
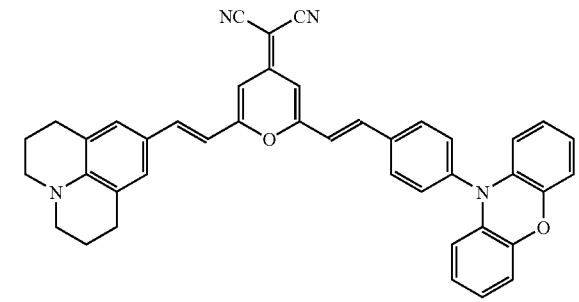
(39)
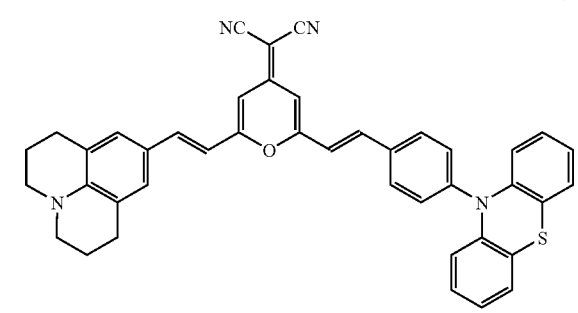
(40)
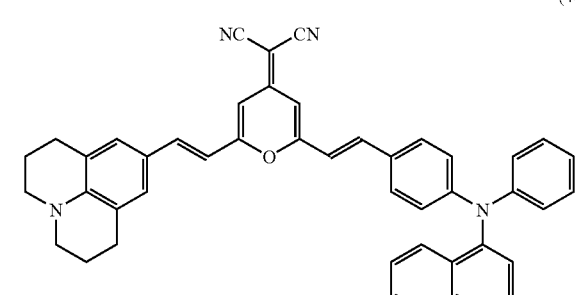
(41)
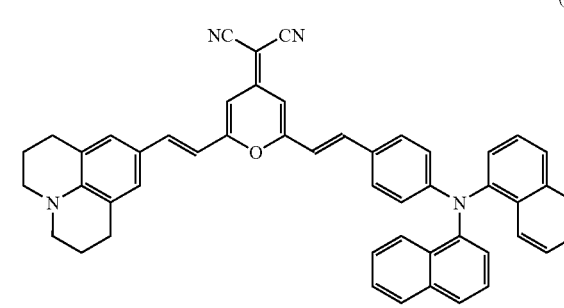
(42)
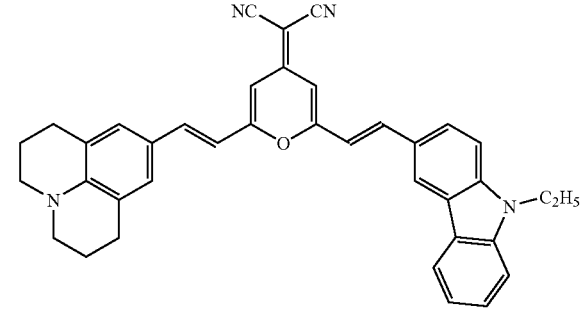

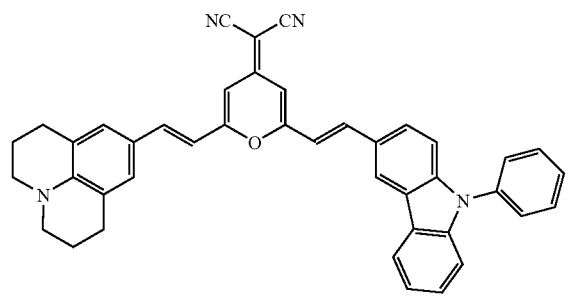
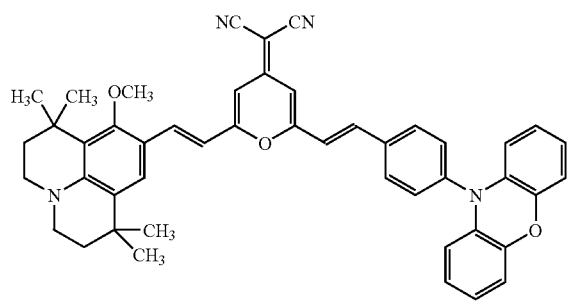
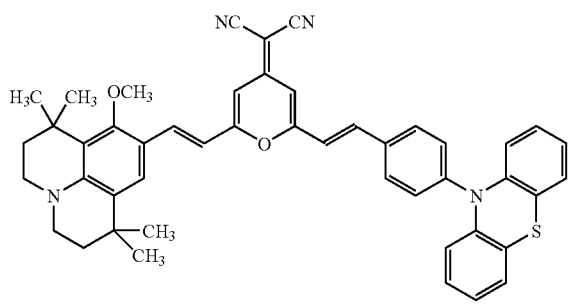
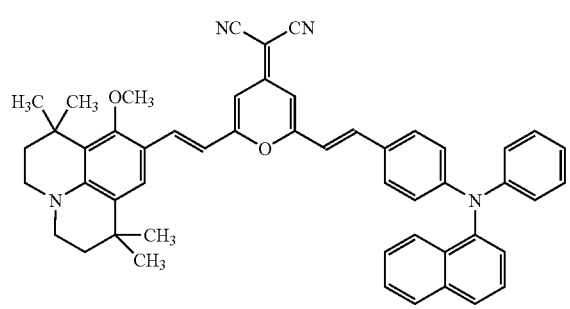
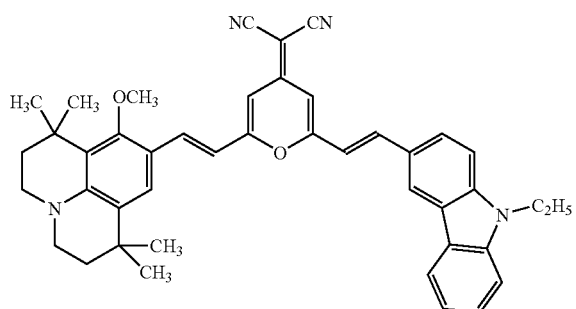
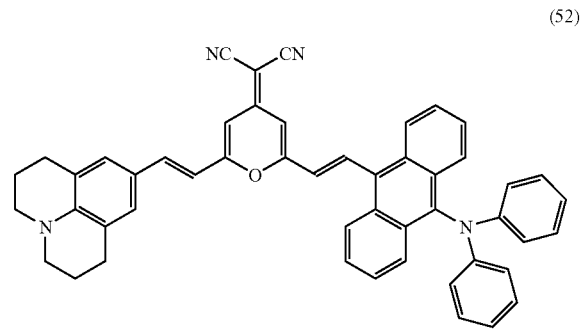

-continued

(53)
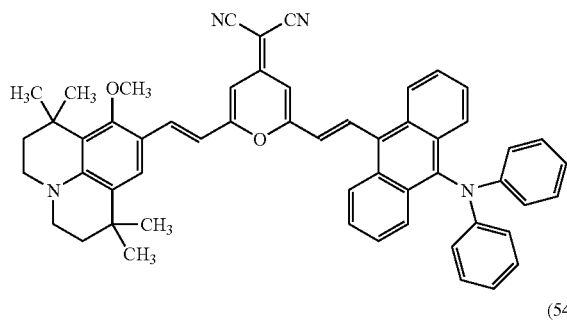

(54)
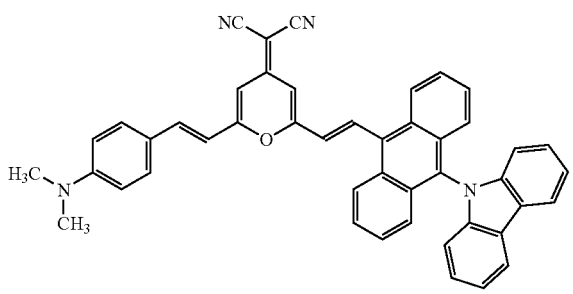

(55)
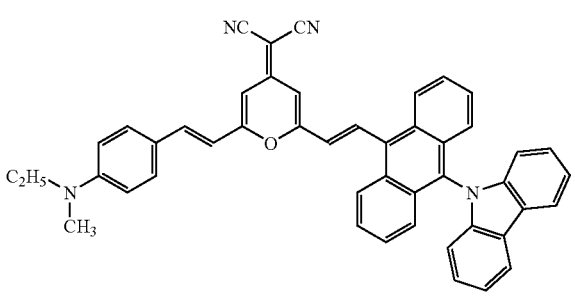

(56)
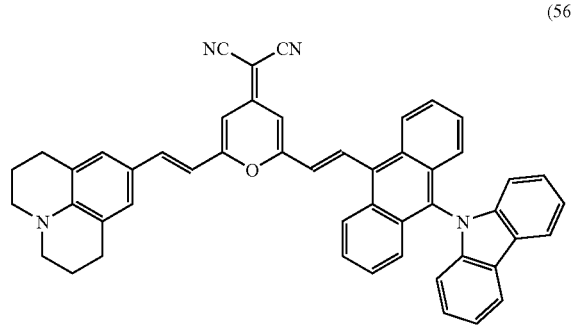

(57)
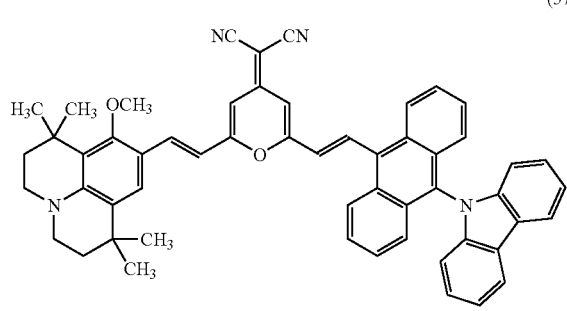

-continued

(58)
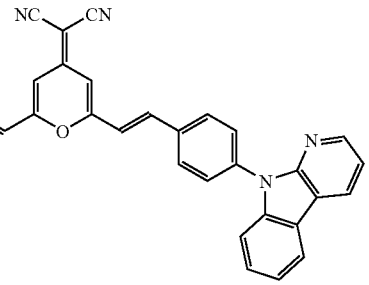

Another feature of the present invention is a method for manufacturing the pyran derivative.

According to one aspect of the present invention, a pyran derivative according to the present invention is manufactured by condensation reaction between a 4-(dicyanomethylene)-2-methyl-4H-pyran derivative having an arylamine skeleton and an arylaldehydes having an arylamine skeleton as represented by the following synthesis scheme (a).

(a)
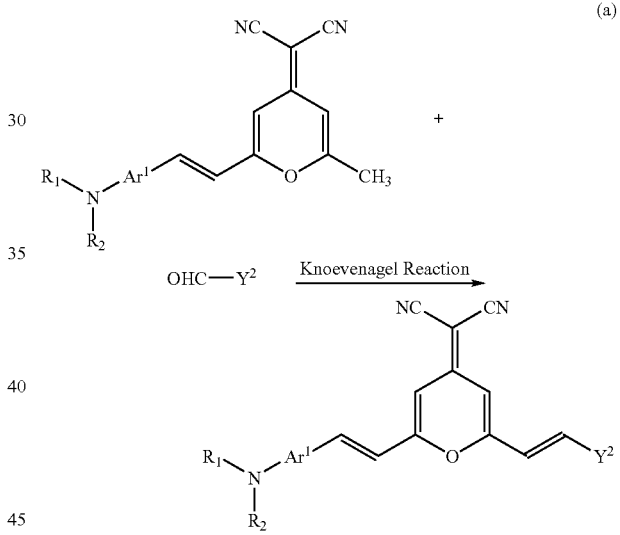

wherein $Y^2$, which is the same as that represented by general formula 2, is represented by general formula 4 or 5; and $Ar^1$, $R^1$, and $R^2$ are the same as those represented by general formula 2.

According to the foregoing synthesis method, a pyran derivative according to the present invention can be obtained in high yields.

Still another feature of the present invention is a light-emitting element containing a pyran derivative that is represented by any one of the above general formulae 1, 2, 6, 10, structural formulae 18 to 58.

As a typical example of a light-emitting element, a light-emitting element having the configuration that a layer containing a light-emitting material is interposed between a pair of electrodes can be nominated. However, a light-emitting element having another configuration can be used.

A pyran derivative according to the invention can be used as a light-emitter since it has hole transportation properties and exhibits long wavelength light of from 560 to 700 nm.

Particularly, a pyran derivative that can exhibit light of from 600 to 660 nm wavelength is suitable for a light-emitter exhibiting reddish emission with good color purity.

Driving voltage for a light-emitting element containing a pyran derivative according to the invention as a light emitter can be reduced since the pyran derivative has carrier transportation properties. A pyran derivative according to the invention can be only used as a light emitter, but the pyran derivative is preferably used as a guest material combined with a host material. Accordingly, a light-emitting element that exhibits long wavelength light may be obtained. In case that a pyran derivative that can exhibit light of from 600 to 660 nm wavelength is used, a light-emitting element that exhibits reddish emission with good color purity can be obtained.

According to the present invention, a pyran derivative that has excellent carrier transportation properties and exhibits long wavelength light can be obtained. Further, a pyran derivative that exhibits reddish emission with good color purity can be obtained. Still further, a pyran derivative according to the invention that can be formed into a film by vapor deposition despite that the pyran derivative is introduced with a sterically bulky alkyl group.

By using a pyran derivative according to the invention, a light-emitting element that is driven at low driving voltage and exhibits long wavelength light can be obtained. Further, a light-emitting element that exhibits reddish emission with good color purity can be obtained.

Moreover, a pyran derivative according to the invention can be obtained in high yields in accordance with a method for manufacturing a pyran derivative according to the invention. Therefore, the cost of raw materials can be reduced for a light-emitting element containing a pyran derivative manufactured by the method according to the invention, a light-emitting device including the light-emitting element, and an electric appliance installed with the light-emitting device. Further, a reddish display image with good color purity can be obtained.

These and other objects, features and advantages of the present invention will become more apparent upon reading of the following detailed description along with the accompanied drawings.

BRIEF DESCRIPTION OF THE DRAWINGS

FIGS. 10A and 10B are explanatory views for showing a light-emitting device applied with the present invention.

DESCRIPTION OF THE INVENTION

Embodiment 1

In Embodiment 1, a light-emitting element including a pyran derivative is explained with reference to FIG. 1.

Figure 1:
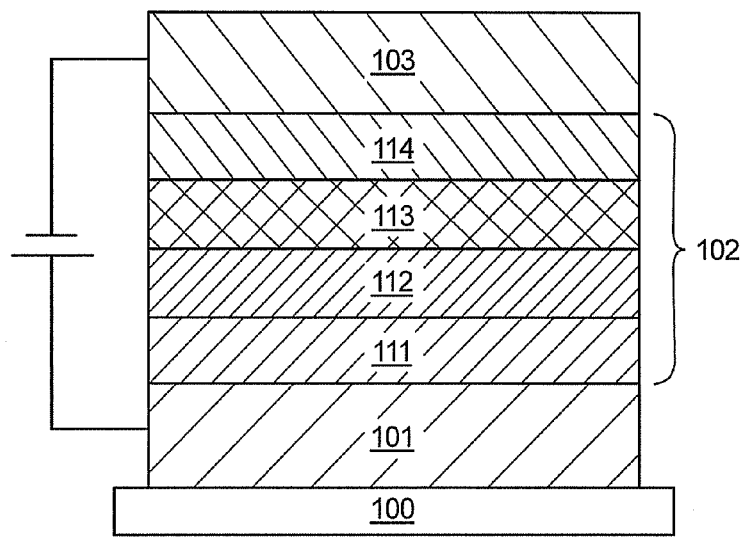
FIG. 1 is an explanatory view for showing a light-emitting element according to the present invention.

As shown in FIG. 1, a first electrode 101 is formed over a substrate 100, and a layer containing a light-emitting material 102 is formed over the first electrode 101, then, a second electrode 103 is formed thereover.

As a material for the substrate 100, any material can be used as long as it is used for the conventional light-emitting element, for example, glass, quartz, transparent plastics, or the like.

In Embodiment 1, the first electrode 101 serves as an anode, and the second electrode 103 serves as a cathode.

Therefore, the first electrode 101 is formed by anode materials. As materials for the anode, metals having large work functions (at least 4.0 eV), alloys, compounds having electrical conduction properties, and mixture of the foregoing materials can be preferably used. As specific examples of the anode materials, ITO (indium tin oxide), IZO (indium zinc oxide) composed of indium oxide mixed with zinc oxide (ZnO) of from 2 to 20%, aurum (Au), platinum (Pt), nickel (Ni), tungsten (W), chromium (Cr), molybdenum (Mo), ferrum (Fe), cobalt (Co), copper (Cu), palladium (Pd), nitrides of metal materials (TiN), or the like can be used.

As cathode materials for forming the second electrode 103, metals having small work functions (at most 3.8 eV), alloys, compounds having electrical conduction properties, mixture of the foregoing materials, or the like is preferably used. As specific examples of the cathode materials, an element of group 1 or 2 of the periodic table, that is, an alkali metal such as lithium (Li), cesium (Cs), or the like; alkali earth metal such as magnesium (Mg), calcium (Ca), strontium (Sr), or the like; and alloys of these elements (Mg: Ag, Al: Li) can be used. In the case that a layer for promoting electron injection is formed between the second electrode 103 and a light-emitting layer so as to be stacked over the second electrode, the second electrode 103 can be formed by conductive materials such as Al, Ag, or ITO regardless of level of the work functions.

As a material for the layer for promoting electron injection, a compound of an alkali metal or an alkali earth metal such as lithium fluoride (LiF), cesium fluoride (CsF), calcium fluoride ($CaF_2$), or the like can be used. Alternatively, a material having electron transportation properties containing an alkali metal or an alkali earth metal, for example, Alq containing magnesium (Mg), or the like can be used.

The above anode and cathode materials are deposited by vapor deposition, sputtering, or the like to form thin films as the first electrode 101 and the second electrode 103.

In a light-emitting element according to the invention, light generated by recombination of carriers within the layer containing a light-emitting material is emitted from either the first electrode 101 or the second electrode 103, or both of the electrodes. When light is emitted from the first electrode 101, the first electrode 101 is formed by materials having light transmission properties. When light is emitted from the second electrode 103, the second electrode 103 is formed by materials having light transmission properties.

The layer containing a light-emitting material 102 is formed by stacking a plurality of layers. In Embodiment 1, the layer containing a light-emitting material 102 is formed by stacking a hole injecting layer 111, a hole transporting layer 112, a light-emitting layer 113, and an electron transporting layer 114.

In this instance, as hole injection materials for forming the hole injecting layer 111, phthalocyanine-based compounds can be efficiently used. For example, phthalocyanine (abbreviated $H_2PC$), copper phthalocyanine (abbreviated Cu—Pc), or the like can be used.

As hole transportation materials for forming the hole transporting layer 112, aromatic amine (that is, the one having a benzene ring-nitrogen bond) based compounds are preferably used. For example, 4,4'-bis[N-(3-methylphenyl)-N-phenyl-amino]-biphenyl (abbreviated TPD), and derivatives thereof such as 4,4'-bis[N-(1-naphthyl)-N-phenyl-amino]-biphenyl (abbreviated a-NPB) are widely used. Also used are star burst aromatic amine compounds such as 4,4'4''-tris(N,N-diphenyl-amino)-triphenyl amine (abbreviated TDATA), and 4,4'4''-tris[N-(3-methylphenyl)-N-phenyl-amino]-triphenyl amine (abbreviated MTDATA).

The light-emitting layer 113 contains a pyran derivative according to the present invention represented by any one of the foregoing general formulae 1, 2, 6, 10, and structural formulae 18 to 58. The light-emitting layer 113 may be formed by co-evaporation of a pyran derivative according to the invention as a guest material and a host material, or vapor deposition of only the pyran derivative according to the invention.

Known compounds can be used as the host materials, for example, 4,4'-bis(N-carbazolyl)-biphenyl (abbreviated CBP), 2,2'2''-(1,3,5-benzenetri-yl)-tris[1-phenyl-1H-benzimidazole] (abbreviated TPBI), 9,10-di(2-naphthyl)anthracene (abbreviated DNA), or the like can be used.

As electron transportation materials for forming the electron transporting layer 114, a metal complex having a quinoline skeleton or a benzoquinoline skeleton such as tris(8-quinolinolate) aluminum (abbreviated $Alq_3$), tris(5-methyl-8-quinolinolate) aluminum (abbreviated $Almq_3$), bis(10-hydroxybenzo[h]-quinolinato) beryllium (abbreviated $BeBq_2$), or the above mentioned BAlq are preferably used. Alternatively, a metal complex having an oxazole based or thiazole based ligand such as bis [2-(2-hydroxyphenyl)-benzooxazolate] zinc (abbreviated $Zn(BOX)_2$), or bis [2-(2-hydroxyphenyl)-benzothiazolate] zinc (abbreviated $Zn(BTZ)_2$) can be used. In addition to the metal complex, 2-(4-biphenyl)-5-(4-tert-butylphenyl)-1,3,4-oxadiazole (abbreviated PBD); 1,3-bis[5-(p-tert-butylphenyl)-1,3,4-oxadiazole-2-yl] benzene (abbreviated OXD-7); 3-(4-tert-butylphenyl)-4-phenyl-5-(4-biphenylyl)-1,2,4-triazole (abbreviated TAZ); 3-(4-tert-butylphenyl)-4-(4-ethylphenyl)-5-(4-biphenylyl)-1,2,4-triazole (abbreviated p-EtTAZ); bathophenanthroline (abbreviated BPhen); bathocuproin (abbreviated BCP); or the like can be used.

Accordingly, a light-emitting element which has the light-emitting layer 113 containing a pyran derivative according to the invention; the hole injecting layer 111 formed by low molecular weight materials; the hole transporting layer 112; and the electron transporting layer 114 can be formed. As materials for the hole injecting layer 111, the hole transporting layer 112, and the electron transporting layer 114, a high molecular material can be used instead of a low molecular material.

The foregoing light-emitting element emits light by current that flows through the light-emitting element by potential difference between the first electrode 101 and the second electrode 103.

Figure 2:
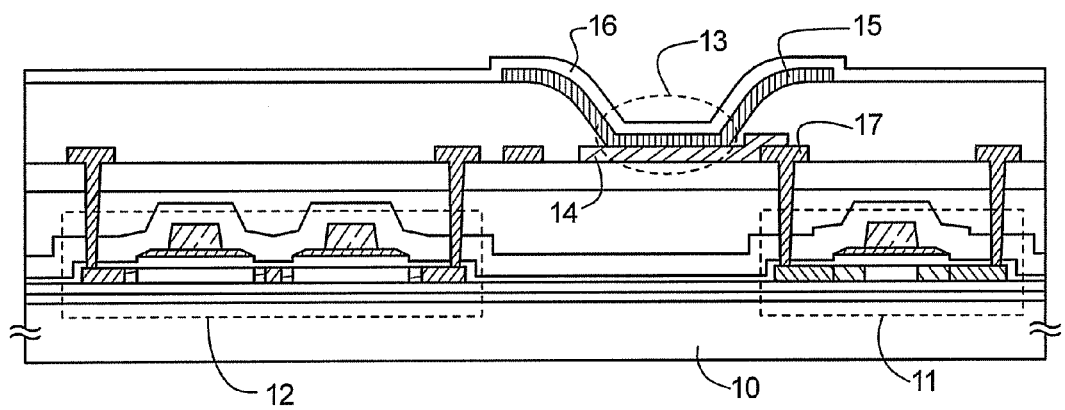
FIG. 2 is an explanatory view for showing a light-emitting element having a light-emitting element according to the present invention.

According to Embodiment 1, a light-emitting element is manufactured over the substrate 100 of glass, quartz, or transparent plastics. By manufacturing a plurality of such light-emitting elements over one substrate, a passive type light-emitting device can be manufactured. Besides the substrate of glass, quartz, or transparent plastics, a light-emitting element formed on a thin film transistor (TFT) array can be manufactured. Further, as shown in FIG. 2, reference numeral 10 denotes a substrate; 11 and 12 enclosed by dotted line, TFTs; 14, a first electrode; 15, a layer containing a light-emitting material; 16, a second electrode; and 17, a wiring. A portion where the first electrode, the layer containing a light-emitting material 15, and the second electrode 16 are overlapped with each other serves as a light-emitting element 13. Accordingly, an active matrix type light-emitting device in which the driving of a light-emitting element is controlled by a TFT can be manufactured. In addition, the structure of the TFT is not especially restricted.

In order to obtain images in a plurality of colors by means of a light-emitting element according to the invention, a layer containing a light-emitting material as an organic compound according to the invention may be formed separately on emission color basis by utilizing masks or banks. In this instance, each the layer formed separately can be formed to have different lamination configuration.

The structure of the layer containing a light-emitting material 102 is not limited to the foregoing structure, and may have another lamination configuration. Other than a light-emitting layer, layers such as an electron injecting layer, an electron transporting layer, a hole blocking layer, a hole transporting layer, or a hole injecting layer can be freely provided. For example, the layer containing a light-emitting material 102 may have the lamination configuration: hole injecting layer/light-emitting layer/electron transporting layer; hole injecting layer/hole transporting layer/light-emitting layer/electron transporting layer; hole injecting layer/hole transporting layer/light-emitting layer/electron transporting layer/electron injecting layer; hole injecting layer/hole transporting layer/light-emitting layer/hole blocking layer/electron transporting layer; hole injecting layer/hole transporting layer/light-emitting layer/hole blocking layer/electron transporting layer/electron injecting layer; or the like.

Driving voltage for a light-emitting element according to the invention can be reduced for the carrier transportation properties of a pyran derivative according to the invention. Since a pyran derivative according to the invention exhibits long wavelength light in the range of from 560 to 700 nm, a light-emitting element according to the invention can be used as a light-emitting element that exhibits long wavelength light in the range of from 560 to 700 nm. In case that a pyran derivative according to the invention that exhibits long wavelength light in the range of from 600 to 660 nm is used, a light-emitting element according to the invention can be used as a light-emitting element that exhibits red light emission with good color purity.

Embodiment 2

In Embodiment 2, a method for forming a pyran derivative represented by the foregoing general formula 6 is explained.

As represented by the following synthesis scheme (b-1), condensation reaction between 4-(dicyanomethylene)-2,6-dimethyl-4H-pyran and p-(dialkylamino) benzaldehyde having an alkylamine skeleton is carried out to synthesize 4-(dicyanomethylene)-2-{p-(dialkylamino)styryl}-6-metyl-4H-pyran having an alkylamino skeleton. Then, as represented by the following synthesis scheme (b-2), condensation reaction between 4-(dicyanomethylene)-2-{p-(dialkylamino)styryl}-6-metyl-4H-pyran and p-(diarylamino)benzaldehyde having an arylamine skeleton is carried to synthesize 4-(dicyanomethylene)-2-{p-(dialkylamino)styryl}-6-{p-(diarylamino)styryl}-4H-pyran.

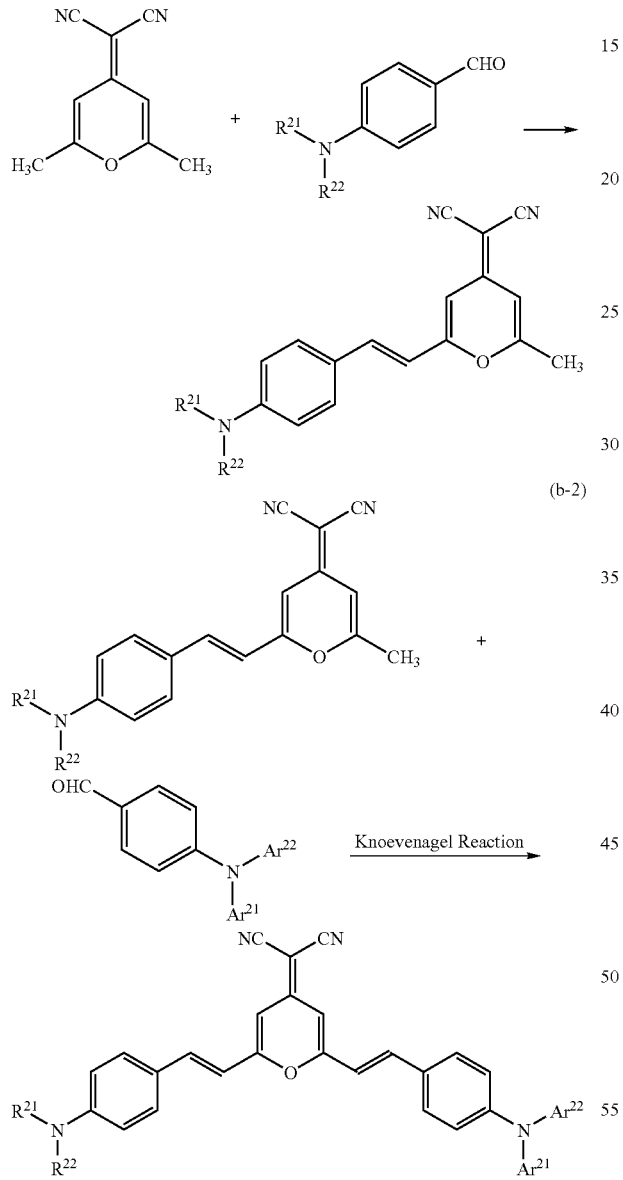

wherein $R^{21}$ and $R^{22}$, each of which may be the same or different, are individually an alkyl group having 1 to 4 carbon atoms; $Ar^{21}$ and $Ar^{22}$, each of which may be the same or different, are individually a substituted or unsubstituted aryl group; and the $Ar^{21}$ and the $Ar^{22}$ may be bonded directly each other or bonded each other via —O— or —S—.

As represented by the foregoing synthesis schemes (b-1), (b-2), condensation reaction between a 4-(dicyanomethylene)-2-methyl-4H-pyran derivative having an alkylamine skeleton and arylaldehydes having an arylamine skeleton results in the formation of a pyran derivative according to the invention in high yields.

As benzaldehydes having an alkylamine skeleton, p-(dimethylamino)benzaldehyde, p-(diethylamino)benzaldehyde, julolidine-9-carbaldehyde, 8-methoxy-1,1,7,7-tetramethyl-julolidine-9-carbaldehyde, and the like can be used. Further, as arylaldehydes having an arylamine skeleton, p-(diphenylamino)benzaldehyde, p-(N-carbazolyl)benzaldehyde, p-{(1-narhtyl)methylamino}benzaldehyde, and the like can be used.

As a dicyanomethylene-4H-pyran derivative having an alkylamine skeleton, the product synthesized in accordance with the procedure as represented by the foregoing synthesis scheme (b-1) can be used, alternatively, a known 4-(dicyanomethylene)-2-methyl-4H-pyran derivative as represented by the following structural formulae 59 to 62.

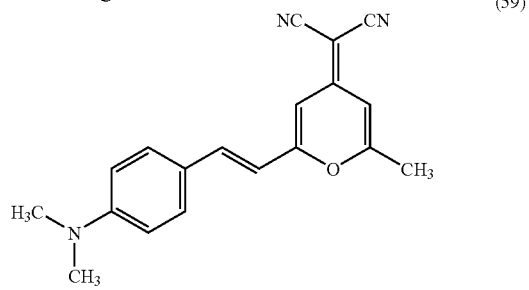

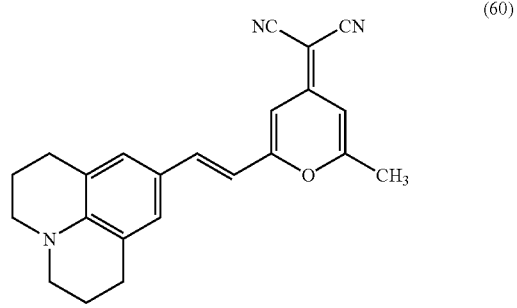

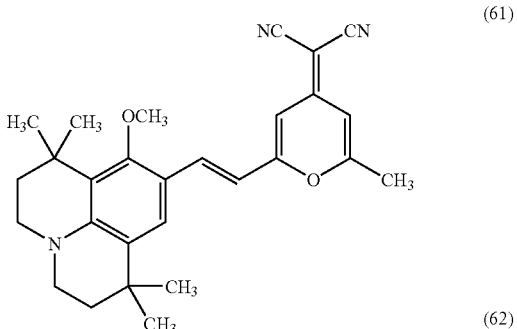

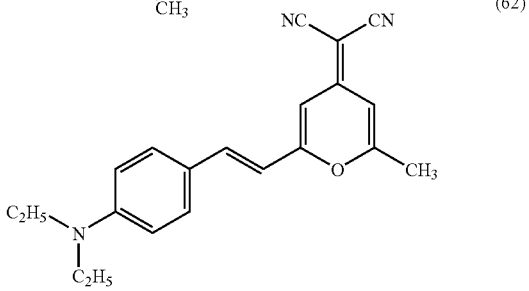

As benzaldehydes having an arylamine skeleton, a product represented by the synthesis scheme (b-1) having a diarylamino group, or p-(alkylarylamino)benzaldehyde having an alkylarylamino group as represented by the following general formula 63 can be used. In this instance, 4-(dicyanomethylene)-2-{p-(dialkylamino)styryl}-6-{p-(alkylarylamino)styryl}-4H-pyran is synthesized.

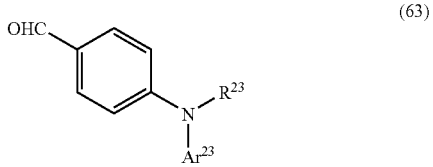

(63)

wherein $Ar^{23}$ is a substituted or unsubstituted aryl group; and $R^{23}$ is an alkyl group having 1 to 4 carbon atoms or a hydrogen atom.

A pyran derivative according to the invention can be formed, as represented by the following synthesis schemes (c-1), (c-2), by synthesizing a 4-(dicyanomethylene)-2-methyl-4H-pyran derivative having an arylamine skeleton to carry out condensation reaction with benzaldehydes having an alkylamine skeleton. However, the synthesis yields of a 4-(dicyanomethylene)-2-methyl-4H-pyran derivative having an arylamine skeleton represented by the synthesis scheme (c-1) is lower than that of a 4-(dicyanomethylene)-2-methyl-4H-pyran derivative having an alkylamine skeleton represented by the synthesis scheme (b-1). Therefore, a pyran derivative according to the invention is preferably formed through the process as represented by the foregoing synthesis scheme (b-2).

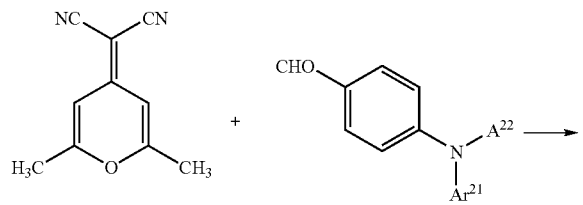

(c-1)

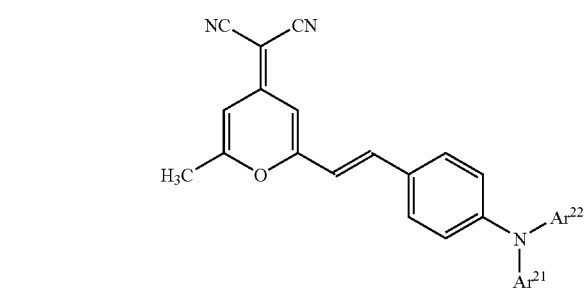

(c-2)

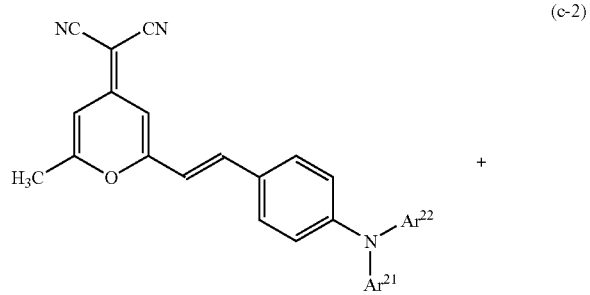

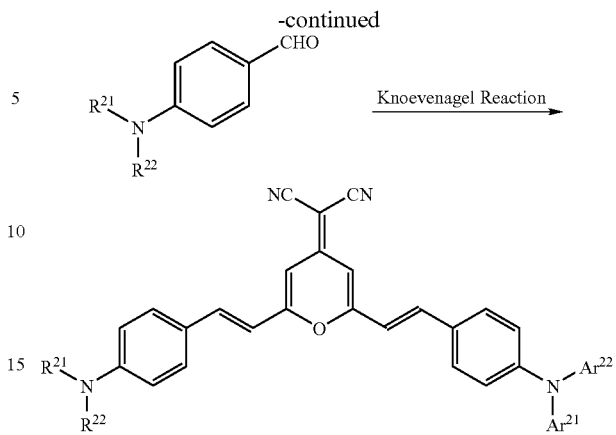

Further, references in the synthesis schemes (c-1) and (c-2) are the same as those in the synthesis schemes (b-1) and (b-2).

EXAMPLE 1

Synthesis Example 1

Preparation of 4-(dicyanomethylene)-2-{p-(dimethylamino)styryl}-6-{p-(diphenylamino)styryl}-4H-pyran as represented by a structural formula 18.

305 mg (1.0 mmol) of 4-(dicyanomethylene)-2-methyl-6-{p-(dimethylamino)styryl}-4H-pyran and 208 mg (1.0 mmol) of p-(diphenylamino)benzaldehyde were added to a three neck distilling flask with capacity of 50 ml. Nitrogen gas stream was delivered into a system. Then, 10 ml of dehydrate acetonitrile and several drops of piperidine were added to the flask. The reaction was refluxed for 9 hours until the reaction was completed. The reaction solvent was cooled to room temperature, and a generated solid was collected. The collected solid was recrystallized from ethyl acetate and hexane to give 354 mg of red powder solid in a yield of 60%. It was confirmed by $^1$H-NMR that the red powder solid was 4-(dicyanomethylene)-2-methyl-6-{p-(dimethylamino)styryl}-4H-pyran.

The result of $^1$H-NMR spectrum was as follows: $^1$H-NMR (300MHz, CDCl$_3$) d ppm: 7.47-7.40 (m, 6H), 7.31 (t, 4H, J=7.8 Hz), 7.17-7.03 (m, 8H), 6.72 (d, 2H), J=8.7 Hz), 6.61-6.55 (m, 3H), 6.51 (d, 1H, J=15.9 Hz), 3.06 (s, 6H).

Figure 3:
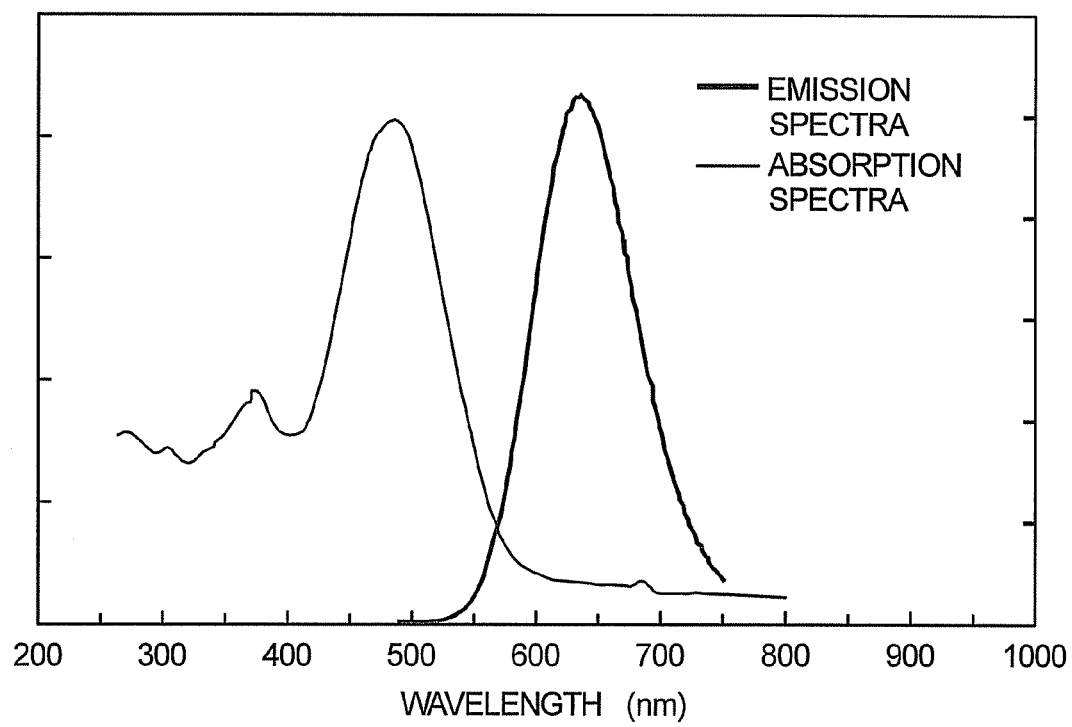
FIG. 3 is emission and absorption spectra of a pyran derivative according to the invention.

FIG. 3 shows absorption and emission spectra of 4-(dicyanomethylene)-2-{p-(dimethylamino)styryl}-6-{p-(diphenylamino)styryl}-4H-pyran in dichloromethane solvent. In the dichloromethane solvent, reddish emission was observed having an emission peak at 636 nm.

Synthesis Example 2

Preparation of 4-(dicyanomethylene)-2-(9-julolidine-yl)ethynyl-6-{p-(diphenylamino)styryl}-4H-pyran as represented by a structural formula 19.

514 mg (1.4 mmol) of 4-(dicyanomethylene)-2-methyl-6-(9-julolidine-yl) ethynyl-4H-pyran and 389 mg (1.4 mmol) of p-(diphenylamino)benzaldehyde were added to a three neck distilling flask with capacity of 50 ml. Nitrogen gas stream was delivered into a system. Then, 10 ml of dehydrate acetonitrile and several drops of piperidine were added to the flask. The reaction was refluxed for 9 hours until the reaction was completed. The reaction solvent was cooled to room temperature, and a generated solid was collected. The collected solid was recrystallized from ethyl acetate and hexane to give 724 mg of black powder solid in a yield of 82%. It was confirmed by $^1$H-NMR that the black powder solid was confirmed that it was 4-(dicyanomethylene)-2-(9-julolidine-yl) ethynyl-6-{p-(diphenylamino)styryl}-4H-pyran.

The result of $^1$H-NMR spectrum was as follows: $^1$H-NMR (300MHz, CDCl$_3$) d ppm: 7.43-7.26 (m, 8H), 7.15-7.00 (m, 10H), 6.58-6.38 (m, 4H), 3.27-3.23 (m, 4H), 2.77-2.73 (m, 4H), 2.00-1.94 (m, 4H).

Figure 4:
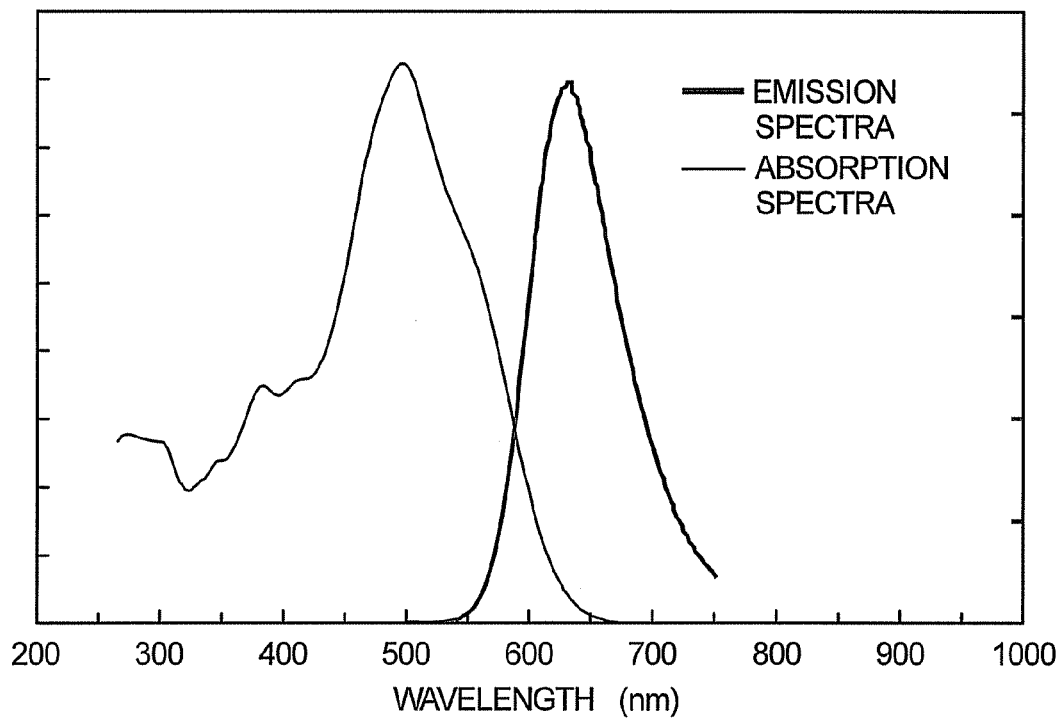
FIG. 4 is emission and absorption spectra of a pyran derivative according to the invention.

FIG. 4 shows absorption and emission spectra of 4-(dicyanomethylene)-2-(9-julolidine-yl) ethynyl-6-{p-(diphenylamino)styryl}-4H-pyran in dichloromethane solvent. In the dichloromethane solvent, reddish emission was observed having an emission peak at 629 nm.

Synthesis Example 3

Preparation of 4-(dicyanomethylene)-2-methyl-6-(8-methoxy-1,1,7,7-tetramethyljulolidine-yl)ethynyl-6-{p-(diphenylamino)styryl}-4H-pyran as represented by a structural formula 20.

194 mg (0.44 mmol) of 4-(dicyanomethylene)-2-methyl-6-(8-methoxy-1,1,7,7-tetramethyljulolidine-yl)ethynyl-4H-pyran and 120 mg (0.44 mmol) of diphenylamino benzaldehyde were added to a three neck distilling flask with capacity of 50 ml. Nitrogen gas stream was delivered into a system. Then, 10 ml of dehydrate acetonitrile and several drops of piperidine were added to the flask. The reaction was refluxed for 9 hours until the reaction was completed. The reaction solvent was cooled to room temperature, and a generated solid was collected. The collected solid was recrystallized from ethyl acetate and hexane to give 100 mg of black powder solid in a yield of 33%. It was confirmed by $^1$H-NMR that the black powder solid was confirmed that it was 4-(dicyanomethylene)-2-(8-methoxy-1,1,7,7-tetramethyljulolidine-yl)ethynyl-6-{p-(dip henylamino)styryl}-4H-pyran.

The result of $^1$H-NMR spectrum was as follows: $^1$H-NMR (300MHz, CDCl$_3$) d ppm: 7.73 (d, 1H, J=16.2 Hz), 7.45 (d, 1H, J=15.9 Hz), 7.38 (d, 2H, J=8.7 Hz), 7.32-7.27 (m, 5H), 7.14-7.07 (m, 6H), 7.03 (d, 2H, J=9.0 Hz), 6.61-6.55 (m, 3H), 6.48 (d, 1H, J=15.6 Hz), 3.83 (s, 3H), 3.28-3.24 (m, 2H), 3.20-3.17 (m, 2H), 1.74-1.70 (m, 4H), 1.41 (s, 6H), 1.30 (s, 6H).

Figure 5:
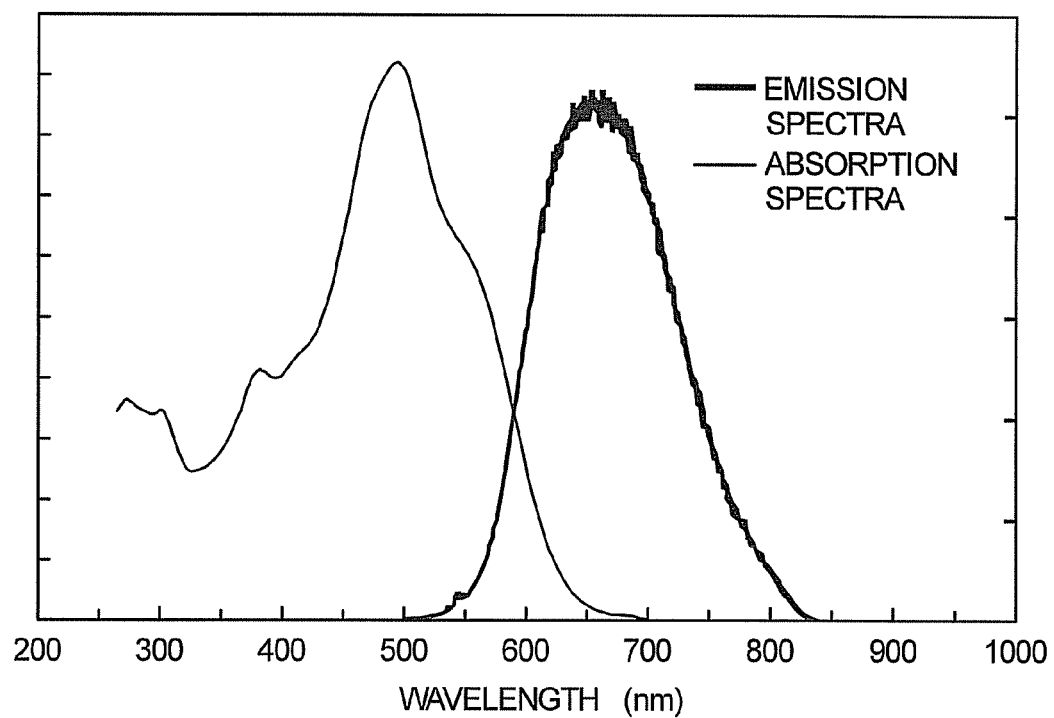
FIG. 5 is emission and absorption spectra of a pyran derivative according to the invention.

FIG. 5 shows absorption and emission spectra of 4-(dicyanomethylene)-2-(8-methoxy-1,1,7,7-tetramethyljulolidine-yl)ethynyl-6-{p-(dip henylamino)styryl}-4H-pyran in dichloromethane solvent. In the dichloromethane solvent, reddish emission was observed having an emission peak at 654 nm.

Synthesis Example 4

Preparation of 4-(dicyanomethylene)-2-{p-(dimethylamino)styryl}-6-{p-(N-carbazolyl)styryl}-4H-pyran as represented by a structural formula 21.

311 mg (1.0 mmol) of 4-(dicyanomethylene)-2-methyl-6-{p-(dimethylamino)styryl}-4H-pyran and 281 mg (1.0 mmol) of p-(diphenylamino)benzaldehyde were added to a three neck distilling flask with capacity of 50 ml. Nitrogen gas stream was delivered into a system. Then, 10 ml of dehydrate acetonitrile and several drops of piperidine were added to the flask. The reaction was refluxed for 9 hours until the reaction was completed. The reaction solvent was cooled to room temperature, and a generated solid was collected. The collected solid was recrystallized from ethyl acetate and hexane to give 360 mg of red powder solid in a yield of 62%. It was confirmed by $^1$H-NMR that the black powder solid was confirmed that it was 4-(dicyanomethylene)-2-{p-(dimethylamino)styryl}-6-{p-(N-carbazolyl)styryl}-4H-pyran.

The result of $^1$H-NMR spectrum was as follows: $^1$H-NMR (300MHz, CDCl$_3$) d ppm: 8.14 (d, 2H, J=7.2 Hz), 7.80 (d, 2H, J=8.7 Hz), 7.67 (d, 2H, J=8.7 Hz), 7.61-7.28 (m, 12H), 6.85-6.52 (m, 4H), 3.06 (s, 6H).

Figure 6:
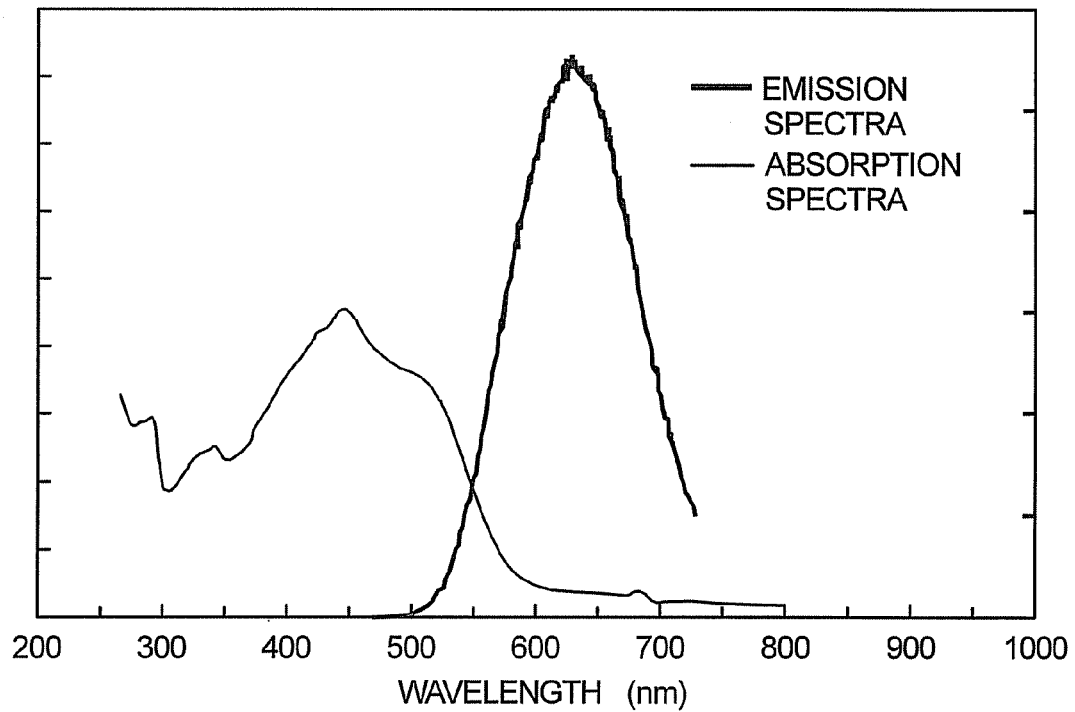
FIG. 6 is emission and absorption spectra of a pyran derivative according to the invention.

FIG. 6 shows absorption and emission spectra of 4-(dicyanomethylene)-2-methyl-6-{p-(dimethylamino)styryl}-4H-pyran in dichloromethane solvent. In the dichloromethane solvent, reddish emission was observed having an emission peak at 632 nm.

Synthesis Example 5

Preparation of 4-(dicyanomethylene)-2-(9julolidine-yl) ethynyl-6-{p-(N-carbazolyl)styryl}-4H-pyran as represented by a structural formula 22.

504 mg (1.4 mmol) of 4-(dicyanomethylene)-2-methyl-6-(9-julolidine-yl)ethynyl-4H-pyran and 382 mg (1.4 mmol) of p-(diphenylamino)benzaldehyde were added to a three neck distilling flask with capacity of 50 ml. Nitrogen gas stream was delivered into a system. Then, 10 ml of dehydrate acetonitrile and several drops of piperidine were added to the flask. The reaction was refluxed for 9 hours until the reaction was completed. The reaction solvent was cooled to room temperature, and a generated solid was collected. The collected solid was recrystallized from ethyl acetate and hexane to give 254 mg of red powder solid in a yield of 30%. It was confirmed by $^1$H-NMR that the black powder solid was confirmed that it was 4-(dicyanomethylene)-2-(9-julolidine-yl)ethynyl-6-{p-(N-carbazolyl)styryl}-4H-pyran.

The result of $^1$H-NMR spectrum was as follows: $^1$H-NMR (300MHz, CDCl$_3$) d ppm: 8.14 (d, 2H, J=7.2 Hz), 7.80 (d, 2H, J=8.1 Hz), 7.66 (d, 2H, J=8.7 Hz), 7.57 (d, 1H, J=16.2 Hz), 7.49-7.28 (m, 7H), 7.05 (s, 2H), 6.81 (d, 1H, J=16.2 Hz), 6.84-6.39 (m, 3H), 3.27-3.23 (m, 4H), 2.77-2.73 (m, 4H), 2.00-1.94 (m, 4H).

Figure 7:
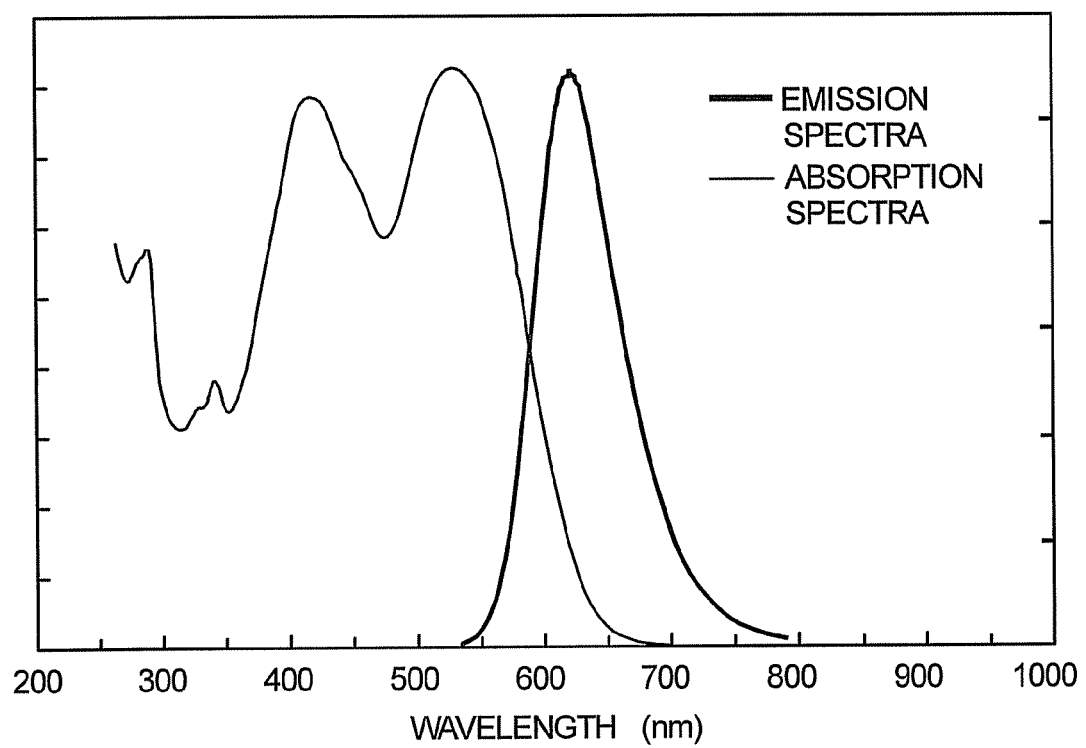
FIG. 7 is emission and absorption spectra of a pyran derivative according to the invention.

FIG. 7 shows absorption and emission spectra of 4-(dicyanomethylene)-2-(9-julolidine-yl)ethynyl-6-{p-(N-carbazolyl)styryl}-4H-pyran in dichloromethane solvent. In the dichloromethane solvent, reddish emission was observed having an emission peak at 623 nm. cl EXAMPLE 2

In Example 2, a light-emitting element according to the present invention including a pyran derivative according to the invention represented by the structural formula 18, 4-(dicyanomethylene)-2-{p-(dimethylamino)styryl}-6-{p-(diphenylamino)styryl}-4H-p yran, and device characteristics of the light-emitting element are explained.

ITO was deposited over a glass substrate by sputtering, and copper phthalocyanine and α-NPB were sequentially deposited by vacuum vapor deposition over the ITO to have thicknesses of 20 nm and 40 nm, respectively. Over the α-NPB, Alq$_3$ containing 1.0 wt % of a pyran derivative according to the invention as represented by the structural formula 18 was deposited to have a thickness of 30 nm by co-evaporation. Over the Alq$_3$, another Alq$_3$ was deposited with a thickness of 20 nm, and CaF$_2$ and aluminum were sequentially deposited. Thus, a light-emitting element according to the invention was manufactured.

Figure 8A:
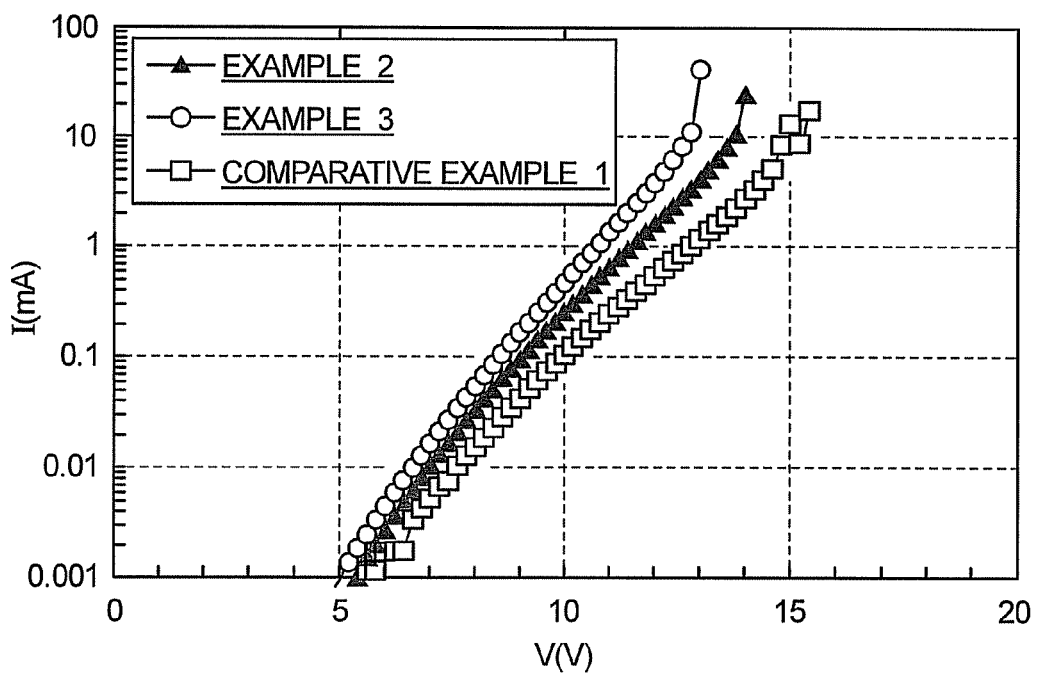
FIGS. 8A and 8B shows current-voltage characteristics and luminance-voltage characteristics of a light-emitting element containing a pyran derivative according to the present invention and Comparative Example 1.
Figure 8B:
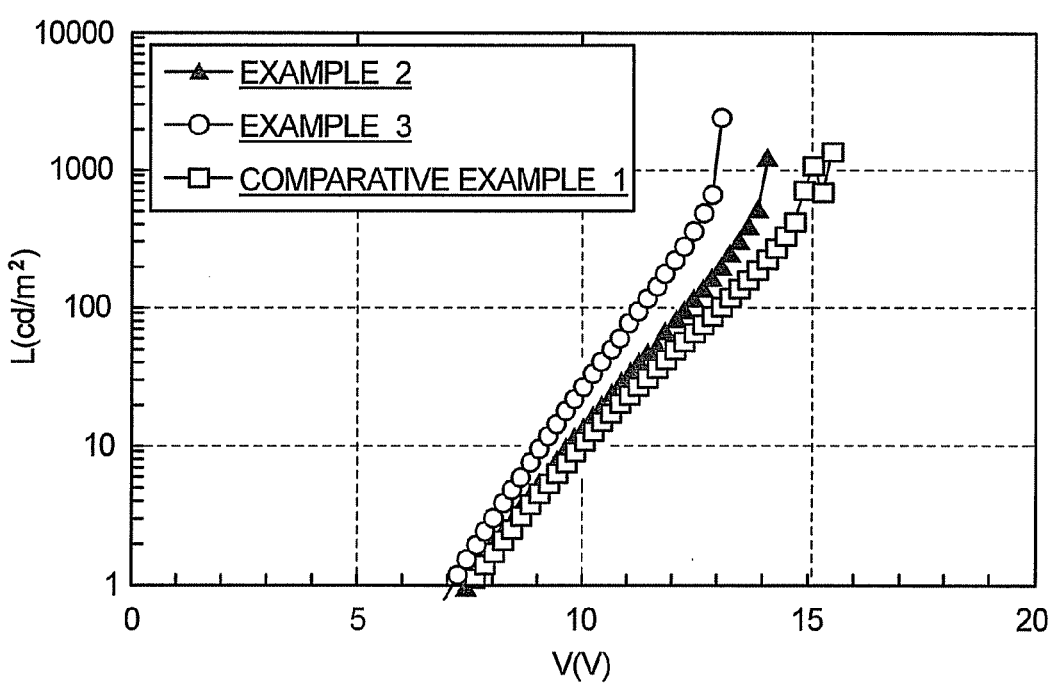
Figure 9:
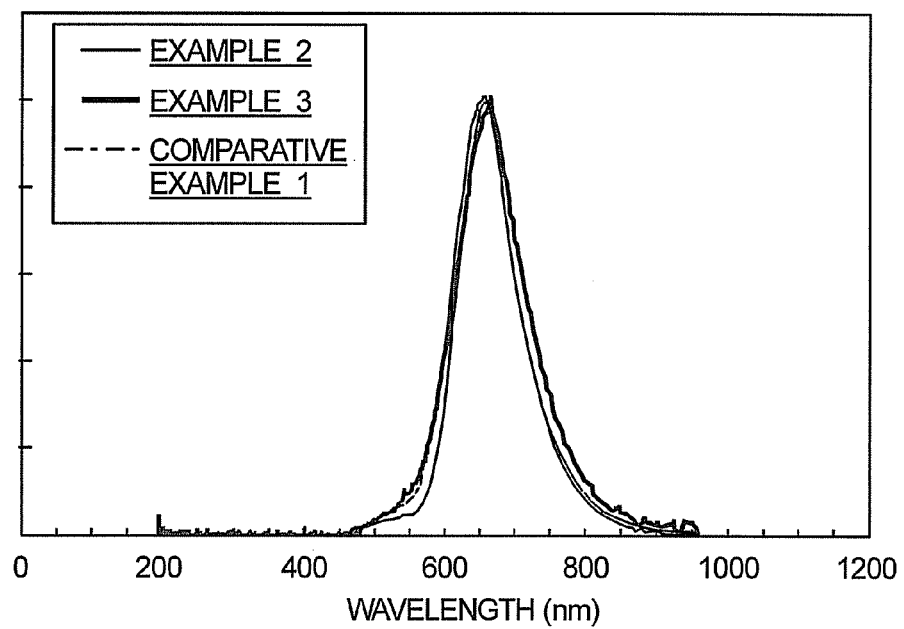
FIG. 9 is an emission spectrum of a light-emitting element containing a pyran derivative according to the present invention and Comparative Example 1.

FIG. 8A shows current-voltage (I-V) characteristics and FIG. 8B shows luminance-voltage (LV) characteristics of thus manufactured light-emitting element according to the invention. The light-emitting element has CIE (x, y) coordinates (0.614, 0.373) at the luminance of approximately 100 cd/m². Reddish emission was observed. FIG. 9 shows the emission spectrum of the light-emitting element.

EXAMPLE 3

In Example 3, a light-emitting element according to the present invention including a pyran derivative according to the invention represented by the structural formula 20, 4-(dicyanomethylene)-2-(8-methoxy-1,1,7,7-tetramethylju-lolidine-yl)ethynyl-6-{p-(dip henylamino)styryl}-4H-pyran, and device characteristics of the light-emitting element are explained.

ITO was deposited over a glass substrate by sputtering, and copper phthalocyanine and a-NPB were sequentially deposited by vacuum vapor deposition over the ITO to have thicknesses of 20 nm and 40 nm, respectively. Over the α-NPB, $Alq_3$ containing 1.0 wt % of a pyran derivative according to the invention as represented by the structural formula 20 was deposited to have a thickness of 30 nm by co-evaporation. Over the $Alq_3$, another $Alq_3$ was deposited with a thickness of 20 nm, and $CaF_2$ and aluminum were sequentially deposited. Thus, a light-emitting element according to the invention was manufactured.

FIG. 8A shows current-voltage (I-V) characteristics and FIG. 8B shows luminance-voltage (L-V) characteristics of thus manufactured light-emitting element according to the invention. The light-emitting element has CIE (x, y) coordinates (0.608, 0.380) at the luminance of approximately 100 cd/m². Reddish emission was observed. FIG. 9 shows the emission spectrum of the light-emitting element.

Comparative Example 1

As a comparative example with a light-emitting element according to the present invention, a light-emitting element including one of bis-pyran derivatives, 4-(dicyanomethyl-ene)-2,6-bis{p-(dimethylamino)styryl}-4H-pyran (Bis-DCM) and the device characteristics are explained. Further, the device configuration is the same as those explained in Examples 2 and 3.

A light-emitting element according to Comparative Example 1 was manufactured as the following procedures. ITO was deposited over a glass substrate by sputtering, and copper phthalocyanine and α-NPB were sequentially deposited by vapor deposition over the ITO to have a thickness of 20 nm and 40 nm, respectively. Over the α-NPB, $Alq_3$ containing 1.0 wt % of BisDCM was deposited to have a thickness of 30 nm by co-evaporation. Over the $Alq_3$, another $Alq_3$ was deposited with a thickness of 20 nm, and $CaF_2$ and aluminum were sequentially deposited.

FIG. 8A shows current-voltage (I-V) characteristics and FIG. 8B shows luminance-voltage (L-V) characteristics of thus manufactured light-emitting element. The light-emitting element has CIE (x, y) coordinates (0.637, 0.352) at the luminance of approximately 100 cd/m². Reddish emission was observed. FIG. 9 shows the emission spectrum of the light-emitting element.

FIG. 8 indicates that the values of current of light-emitting elements according to Examples 2 and 3 are higher than that of a light-emitting element according to Comparative Example 1 at the same amount of applied current. Therefore, a pyran derivative according to the invention has high carrier transportation properties. FIG. 8B indicates that the required voltages of light-emitting elements according to Examples 2 and 3 for obtaining the same level of luminance as that of a light-emitting element according to Comparative Example 1 are lower than that thereof. That is, light-emitting elements according to Examples 2 and 3 are driven at lower drive voltage than that required from a light-emitting element according to Comparative Example 1. Further, FIG. 9 indicates that light-emitting elements according to Examples 2 and 3 can emit the same level of long wavelength light as that of a light-emitting element according to Comparative Example 1.

EXAMPLE 4

In Example 4, a light-emitting device having a pixel portion composed of light-emitting elements according to the present invention is explained with reference to FIGS. 10A and 10B. FIG. 10A is a top view of a light-emitting device. FIG. 10B is a cross-sectional view of FIG. 10A taken along line A-A'. Reference numeral 401 indicated by dotted line denotes a driver circuit portion (source side driver circuit); 402, a pixel portion; 403, a driver circuit portion (gate side driver circuit); 404, a sealing substrate; and 405, a sealing agent. Reference 407 denotes space surrounded by the sealing agent 405.

A lead wiring 408 is a wiring for transmitting signals to be inputted to the source side driver circuit 401 and the gate side driver circuit 403. The lead wiring 408 receives video signals or clock signals from an FPC (flexible printed circuit) 409 serving as an external input terminal. A PWB (printed wirings board) may be attached to the FPC. As used herein, the term "light-emitting device" refers to not only a main body of a light-emitting device, but also a light-emitting device attached with an FPC or a PWB.

Then, a cross-sectional structure will be explained with reference to FIG. 10B. A driver circuit portion and a pixel portion are formed over a substrate 410. In FIG. 10B, the source side driver circuit 401 and the pixel portion 402 are illustrated as a driver circuit portion.

The source side driver circuit 401 is provided with a CMOS circuit formed by combining an n-channel TFT 423 and a p-channel TFT 424. A TFT for forming a driver circuit may be formed by a known CMOS, PMOS, or NMOS circuit. In Example 4, a driver integrated type, that is, a driver circuit is formed over a substrate, is described, but not exclusively, the driver circuit can be formed outside instead of over a substrate.

The pixel portion 402 is composed of a plurality of pixels including a switching TFT 411, a current control TFT 412, and a first electrode 413 connected to the drain of the current control TFT 412. Insulator 414 is formed to cover the edge of the first electrode 413. Here, the insulator 414 is formed by a positive type photosensitive acrylic resin film.

In order to make favorable coverage, an upper edge portion or a lower edge portion of the insulator 414 is formed to have a curved face having a radius of curvature. For example, in case that positive type photosensitive acrylic is used as a material for the insulator 414, only upper edge portion of the insulator 414 is preferably having a radius of curvature (from 0.2 to 3 μm). As the insulator 414, either a negative type photosensitive resin that becomes insoluble to etchant by light or a positive type photosensitive resin that becomes dissoluble to etchant by light can be used.

A layer containing a light-emitting material 416 and a second electrode 417 are formed over the first electrode 413. As a material for the first electrode 413 serving as an anode, a material having a high work function is preferably used. For example, a single layer such as an indium tin oxide (ITO) film, an indium zinc oxide (IZO) film, a titanium nitride film, a chromic film, a tungsten film, a zinc film, or a platinum film; and a lamination layer of the foregoing single layer and a film containing titanium nitride and aluminum as its main components; or a three lamination layer of the foregoing single layer, the film containing titanium nitride and aluminum as its main components, and a titanium nitride film can be used. In case that the first electrode 413 is formed into a lamination layer, the first electrode 413 can be formed to have low resistance as a wiring, make good ohmic contact, and serve as an anode.

The layer containing a light-emitting material 416 is formed by vapor deposition using an evaporation mask, or ink jetting. The layer containing a light-emitting material 416 includes partly a pyran derivative according to the invention. Another material that can be used for the layer containing a light-emitting material 416, either a low molecular material or a high molecular material can be used. As a material for the layer containing a light-emitting material 416, a single layer or a lamination layer of organic compounds is generally used. However, inorganic compounds may be partly contained in film of organic compounds in Example 4.

In order to obtain images in a plurality of colors by means of a light-emitting element according to the invention, a layer containing a pyran derivative according to the invention as a light-emitting material may be formed separately on emission color basis by utilizing masks or bank layers. In this instance, each the layer formed separately can be formed to have different lamination configuration.

As the second electrode (cathode) 417 formed over the layer containing a light-emitting material 416, a material having a small work function (Al, Ag, Li, Ca; or alloys of these elements such as Mg: Ag, Mg: In, or Al: Li; $CaF_2$; or CaN) can be used. In case that light generated in the layer containing a light-emitting material 416 is emitted passing through the second electrode (cathode) 417, the second electrode (cathode) 417 may be formed to have a lamination layer of a thin metal film having a thin thickness and a transparent conductive film (indium tin oxides (ITO), alloys of indium zinc oxide ($In_2O_3$—ZnO), zinc oxides (ZnO), or the like).

By pasting the sealing substrate 404 onto the substrate 410 with the sealing agent 405, the light-emitting element 418 is encapsulated into the space 407 surrounded by the substrate 410, the sealing substrate 404, and the sealing agent 405. The space 407 may be filled with an inert gas (nitrogen, argon, or the like), or the sealing agent 405.

Epoxy resin is preferably used for the first sealing agent 405. It is desirable that the material inhibits moisture or oxygen as possible. As a material for the sealing substrate 404, a plastic substrate formed by FRP (Fiberglass-Reinforced Plastics), PVF (polyvinyl fluoride), Myler, polyester, acrylic, or the like can be used besides a glass substrate or a quartz substrate.

Thus, a light-emitting device having a light-emitting element according to the invention can be obtained.

EXAMPLE 5

Hereinafter, electric appliances manufactured by practicing the present invention are explained with reference to FIGS. 11A to 11F.

Figure 11A:
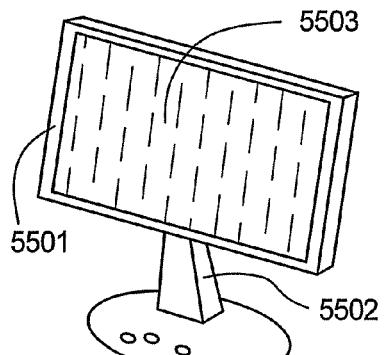
FIGS. 11A to 11F are explanatory views for showing electric appliances applied with the present invention.

FIG. 11A shows a display device composed of a frame 5501; a support 5502; and a display portion 5503. The display device can be completed by installing a light-emitting device described in Example 4 to the display device.

Figure 11B:
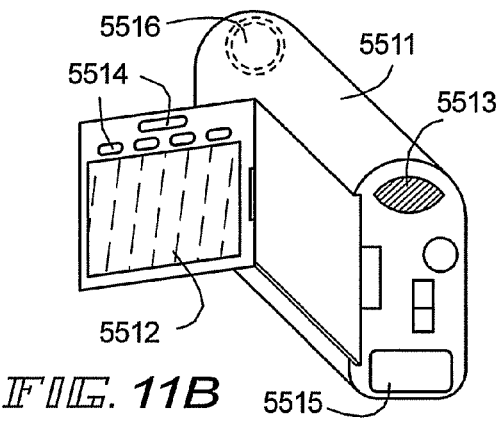

FIG. 11B shows a video camera composed of a main body 5511; a display portion 5512; a voice input portion 5513; operation switches 5514; a battery 5515; an image reception area 5516; and the like. The video camera can be completed by installing a light-emitting device described in Example 4 to the video camera.

Figure 11C:
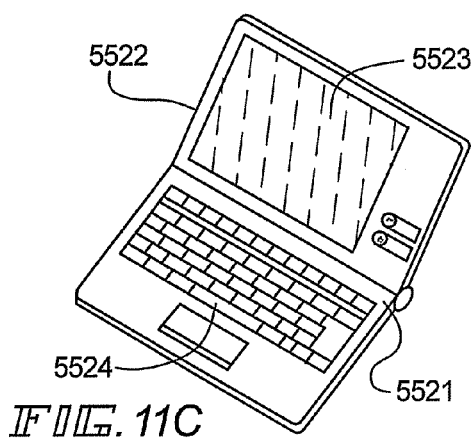

FIG. 11C shows a laptop computer manufactured according to the invention composed of a main body 5521; a frame 5522; a display portion 5523; a keyboard 5524; and the like. The laptop computer can be completed by installing a light-emitting device described in Example 4 to the laptop computer.

Figure 11D:
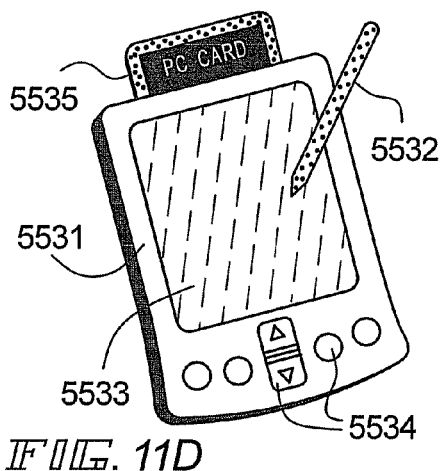

FIG. 11D shows a personal digital assistant (PDA) manufactured according to the invention composed of a main body 5531; a display portion 5533; an external interface 5535; operation switches 5534; and the like. The personal digital assistant also has a stylus 5532 as an attachment for the machine. The personal digital assistant can be completed by installing a light-emitting device described in Example 4 to the personal digital assistant.

Figure 11E:
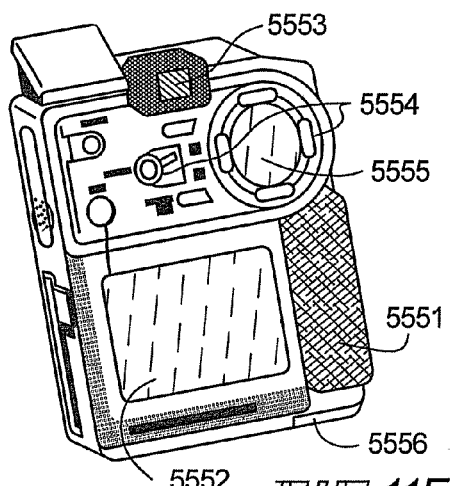

FIG. 11E shows a digital camera composed of a main body 5551; a display portion (A) 5552; an eye piece portion 5553; operation switches 5554; a display portion (B) 5555; a battery 5556; and the like. The digital camera can be completed by installing a light-emitting device described in Example 4 to the digital camera.

Figure 11F:
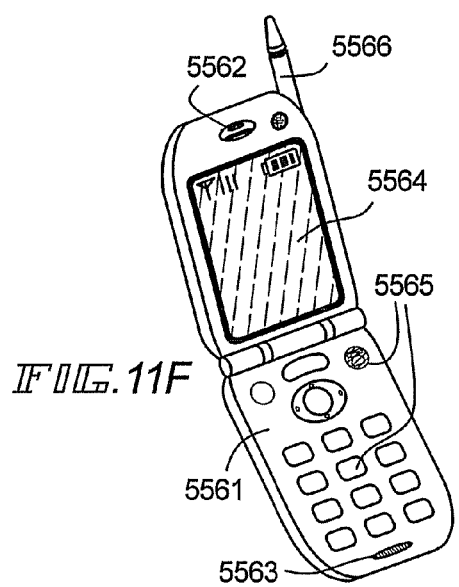

FIG.11F shows a cellular phone manufactured according to the invention composed of a main body 5561; a voice output portion 5562; a voice input portion 5563; a display portion 5564; operation switches 5565; an antenna 5566; and the like. The cellular phone can be completed by installing a light-emitting device described in Example 4 to the cellular phone.

Although the present invention has been fully described by way of examples with reference to the accompanying drawings, it is to be understood that various changes and modifications will be apparent to those skilled in the art. Therefore, unless otherwise such changes and modifications depart from the scope of the present invention hereinafter described, they should be construed as being included therein.

What is claimed is:

1. A pyran derivative represented by general formula 1:

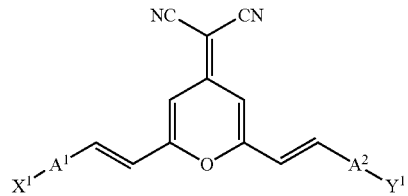

wherein $A^1$ and $A^2$ are individually an aromatic ring, and at least one of $A^1$ and $A^2$ is represented by general formula 1-1, (1-1)

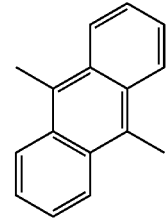

wherein $X^1$ is a dialkylamino group; and $Y^1$ is a diarylamino group or an alkylarylamino group.

2. A pyran derivative represented by general formula 2:

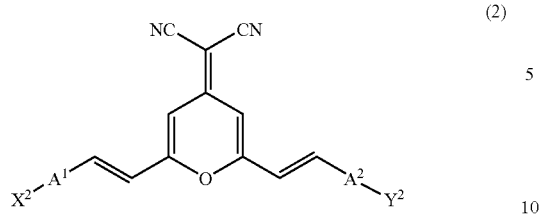
(2)

wherein $A^1$ and $A^2$ are individually an aromatic ring, and at least one of $A^1$ and $A^2$ is represented by general formula 2-1,

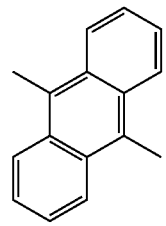
(2-1)

wherein $X^2$ is represented by general formula 3; and $Y^2$ is represented by general formula 4 or 5,

(3)

wherein $R^1$ and $R^2$, each of which may be the same or different, are individually an alkyl group having 1 to 4 carbon atoms;

(4)

wherein $Ar^3$ and $Ar^4$, each of which may be the same or different, are individually a substituted or unsubstituted aryl group or a heterocyclic group; and a pair of $Ar^3$ and $Ar^4$ may be bonded directly with each other or bonded with each other via —O— or —S—,

(5)

wherein $Ar^6$ is a substituted or unsubstituted aryl group; and $R^3$ is an alkyl group having 1 to 4 carbon atoms or a hydrogen atom.

3. A pyran derivative represented by general formula 6:

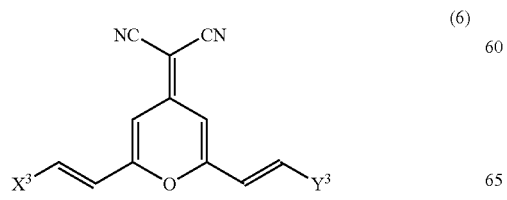
(6)

wherein $X^3$ is represented by general formula 7; and $Y^3$ is represented by general formula 8 or 9,

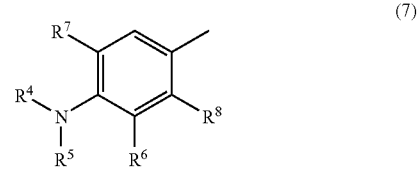
(7)

wherein $R^4$ and $R^5$, each of which may be the same or different, are individually an alkyl group having 1 to 4 carbon atoms,

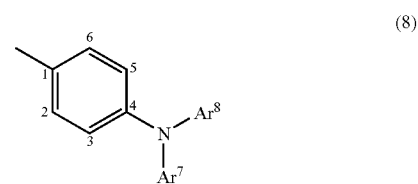
(8)

wherein $Ar^6$ and $Ar^7$, each of which may be the same or different, are individually a substituted or unsubstituted aryl group or a heterocyclic group; a pair of $Ar^6$ and $Ar^7$ may be directly bonded with each other or bonded with each other via —O— or —S—,

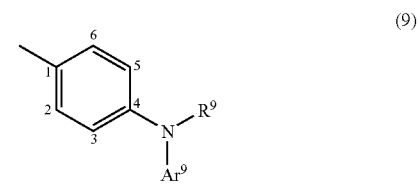
(9)

wherein $Ar^9$ is a substituted or unsubstituted aryl group; and $R^9$ is an alkyl group having 1 to 4 carbon atoms or a hydrogen atom.

4. A pyran derivative represented by general formula 10:

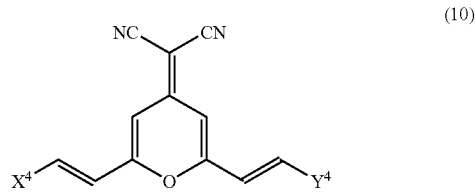
(10)

wherein $X^4$ is represented by general formula 11; and $Y^4$ is represented by any one of general formulae 13 to 15,

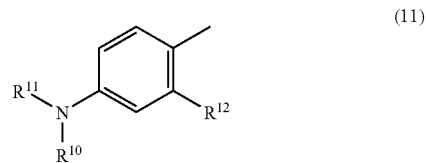
(11)

wherein $R^{10}$ and $R^{11}$, each of which may be the same or different, are individually an alkyl group having 1 to 4 carbon atoms,

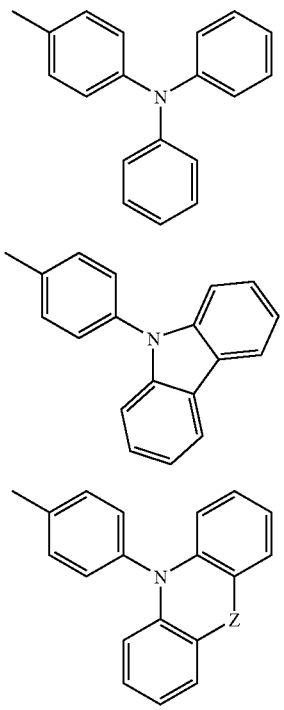

wherein Z is an oxygen atom (O) or a sulfur atom (S).

5. A method for manufacturing a pyran derivative according to claim 3, comprising the step of:
condensing 4-(dicyanomethylene)-2-{p-(dialkylamino) styryl}-6-methyl-4H-pyran and p-(diarylamino)benzaldehyde.

6. A method for manufacturing a pyran derivative according to claim 4, comprising the step of:
condensing 4-(dicyanomethylene)-2-{p(dialkylamino) styryl}-6-methyl-4H-pyran and p-(diarylamino)benzaldehyde.

7. A method for manufacturing a pyran derivative according to claim 3, comprising the steps of:
condensing 4-(dicyanomethylene)-2,6-dimethyl-4H-pyran and p-(dialkylamino)benzaldehyde to synthesize 4-(dicyanomethylene)-2-{p-(dialkylamino)styryl}-6-methyl-4H-pyran; and
condensing the 4-(dicyanomethylene)-2-{p-(dialkylamino)styryl}-6-methyl-4H-pyran and p-(diarylamino)benzaldehyde.

8. A method for manufacturing a pyran derivative according to claim 4, comprising the steps of:
condensing 4-(dicyanomethylene)-2,6-dimethyl-4H-pyran and p-(dialkylamino)benzaldehyde to synthesize 4-(dicyanomethylene)-2-{p-(dialkylamino)styryl}-6-methyl-4H-pyran; and
condensing the 4-(dicyanomethylene)-2-{p-(dialkylamino)styryl}-6-methyl-4H-pyran and p-(diarylamino)benzaldehyde.

9. A light-emitting element having the pyran derivative according to any one of claims 1 to 4.

10. A light-emitting element having a layer containing the pyran derivative according to any one of claims 1 to 4 between a pair of electrodes.

11. A light-emitting element having the pyran derivative according to any one of claims 1 to 4 as a light emitter.

12. A light-emitting device having the pyran derivative any one of claims 1 to 4 in a light emitting element.

13. An electric appliance comprising:
a display portion having a light emitting element;
wherein the light emitting element comprises a light emitting layer having a pyran derivative,
wherein the pyran derivative is represented by general formula 1,

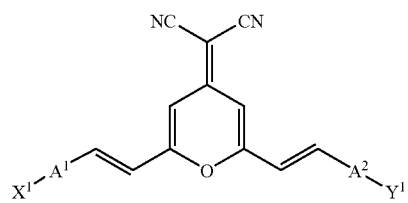

wherein $A^1$ and $A^2$ are individually an aromatic ring, and at least one of $A^1$ and $A^2$ is represented by general formula 1-1,

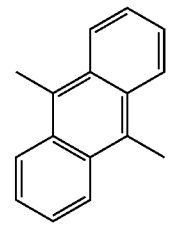

wherein $X^1$ is a dialkylamino group; and $Y^1$ is a diarylamino group or an alkylarylamino group.

14. An electric appliance comprising:
a display portion having a light emitting element;
wherein the light emitting element comprises a light emitting layer having a pyran derivative,
wherein the pyran derivative is represented by general formula 2,

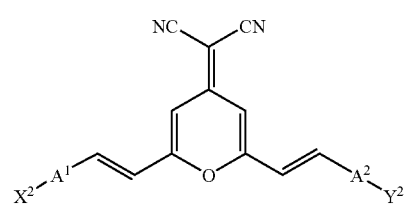

wherein $A^1$ and $A^2$ are individually an aromatic ring, and at least one of $A^1$ and $A^2$ is represented by general formula 2-1,

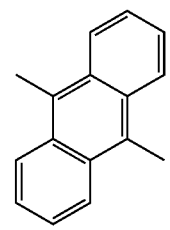

wherein $X^2$ is represented by general formula 3; and $Y^2$ is represented by general formula 4 or 5,

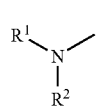
(3)

wherein $R^1$ and $R^2$, each of which may be the same or different, are individually an alkyl group having 1 to 4 carbon atoms;

(4)

wherein $Ar^3$ and $Ar^4$ each of which may be the same or different, are individually a substituted or unsubstituted aryl group or a heterocyclic group; and a pair of $Ar^3$ and $Ar^4$ may be bonded directly with each other or bonded with each other via —O— or —S—,

(5)

wherein $Ar^6$ is a substituted or unsubstituted aryl group; and $R^3$ is an alkyl group having 1 to 4 carbon atoms or a hydrogen atom.

15. An electric appliance comprising:
a display portion having a light emitting element;
wherein the light emitting element comprises a light emitting layer having a pyran derivative,
wherein the pyran derivative is represented by general formula 6,

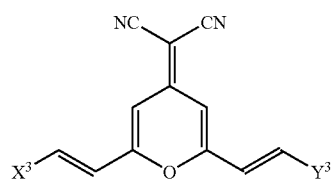
(6)

wherein $X^3$ is represented by general formula 7; and $Y^3$ is represented by general formula 8 or 9,

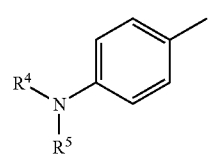
(7)

wherein $R^4$ and $R^5$, each of which may be the same or different, are individually an alkyl group having 1 to 4 carbon atoms,

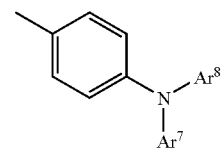
(8)

wherein $Ar^6$ and $Ar^7$, each of which may be the same or different, are individually a substituted or unsubstituted aryl group or a heterocyclic group; a pair of $Ar^6$ and $Ar^7$ may be directly bonded with each other or bonded with each other via —O— or —S—,

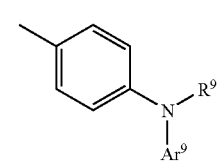
(9)

wherein $Ar^9$ is a substituted or unsubstituted aryl group; and $R^9$ is an alkyl group having 1 to 4 carbon atoms or a hydrogen atom.

16. An electric appliance comprising:
a display portion having a light emitting element;
wherein the light emitting element comprises a light emitting layer having a pyran derivative,
wherein the pyran derivative is represented by general formula 10,

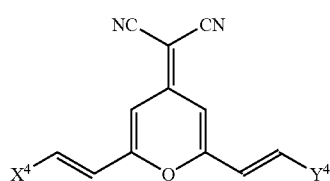
(10)

wherein $X^4$ is represented by general formula 11; and $Y^4$ is represented by any one of general formulae 13 to 15,

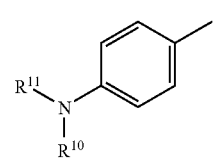
(11)

wherein $R^{10}$ and $R^{11}$, each of which may be the same or different, are individually an alkyl group having 1 to 4 carbon atoms,

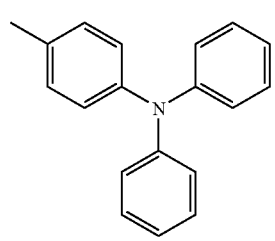
(13)

-continued

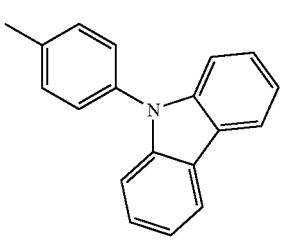

(14)

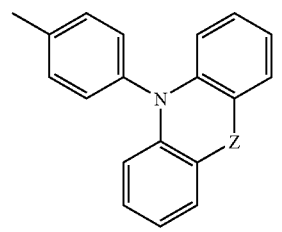

(15)

wherein Z is an oxygen atom (O) or a sulfur atom (S).

17. An electronic appliance according to claim 13, wherein the electronic appliance is selected from the group consisting of a display device, a video camera, a laptop computer, a personal digital assistance, a digital camera and a cellular phone.

18. An electronic appliance according to claim 14, wherein the electronic appliance is selected from the group consisting of a display device, a video camera, a laptop computer, a personal digital assistance, a digital camera and a cellular phone.

19. An electronic appliance according to claim 15, wherein the electronic appliance is selected from the group consisting of a display device, a video camera, a laptop computer, a personal digital assistance, a digital camera and a cellular phone.

20. An electronic appliance according to claim 16, wherein the electronic appliance is selected from the group consisting of a display device, a video camera, a laptop computer, a personal digital assistance, a digital camera and a cellular phone.

* * * * *